United States Patent
Gerdes et al.

(10) Patent No.: US 7,361,471 B2
(45) Date of Patent: Apr. 22, 2008

(54) NUCLEIC ACID ARCHIVING

(75) Inventors: John C. Gerdes, Denver, CO (US); Jeffery M. Marmaro, Aurora, CO (US); Jeffrey T. Ives, Arvada, CO (US); Christopher A. Roehl, Tampa, FL (US)

(73) Assignee: Applera Corporation, Foster City, CA (US)

(*) Notice: Subject to any disclaimer, the term of this patent is extended or adjusted under 35 U.S.C. 154(b) by 36 days.

(21) Appl. No.: 11/436,919

(22) Filed: May 18, 2006

(65) Prior Publication Data

US 2006/0211034 A1 Sep. 21, 2006

Related U.S. Application Data

(60) Division of application No. 10/690,359, filed on Oct. 21, 2003, now Pat. No. 7,087,387, which is a division of application No. 09/944,604, filed on Aug. 31, 2001, now Pat. No. 6,872,527, which is a continuation-in-part of application No. 09/061,757, filed on Apr. 16, 1998, now Pat. No. 6,291,166.

(60) Provisional application No. 60/041,999, filed on Apr. 16, 1997.

(51) Int. Cl.
C12Q 1/68 (2006.01)
C12P 19/34 (2006.01)
C07H 21/02 (2006.01)
C07H 21/04 (2006.01)

(52) U.S. Cl. .................. 435/6; 435/91.2; 536/23.1; 536/24.3

(58) Field of Classification Search .............. 435/6, 435/91.2; 536/23.1, 24.3
See application file for complete search history.

(56) References Cited

U.S. PATENT DOCUMENTS

| 5,234,809 | A | 8/1993 | Boom et al. |
|---|---|---|---|
| 5,405,951 | A | 4/1995 | Woodard |
| 5,438,127 | A | 8/1995 | Woodard et al. |
| 5,438,129 | A | 8/1995 | Woodard et al. |
| 5,503,816 | A | 4/1996 | Woodard et al. |
| 5,506,105 | A | 4/1996 | Haydock et al. |
| 5,523,392 | A | 6/1996 | Woodard et al. |
| 5,525,319 | A | 6/1996 | Woodard et al. |
| 5,578,179 | A | 11/1996 | Demorest et al. |
| 5,629,214 | A | 5/1997 | Crosby |
| 5,674,997 | A | 10/1997 | Woodard et al. |
| 5,863,502 | A | 1/1999 | Southgate et al. |
| 5,863,801 | A | 1/1999 | Southgate et al. |
| 5,939,259 | A | 8/1999 | Harvey et al. |
| 6,043,080 | A | 3/2000 | Lipshutz et al. |
| 6,066,448 | A | 5/2000 | Wohlstadter et al. |
| 6,180,778 | B1 | 1/2001 | Bastian et al. |
| 6,265,557 | B1 * | 7/2001 | Diamond et al. .......... 536/23.1 |
| 6,291,166 | B1 * | 9/2001 | Gerdes et al. .................. 435/6 |
| 6,872,527 | B2 | 3/2005 | Gerdes et al. |

OTHER PUBLICATIONS

Chamberlain et al. Multiplex PCR for the Diagnosis of Duchenne Muscular Dystrophy. Chapter 33 PCR Protocols : A Guide to Methods and Applications pp. 272-281 (1990).*
Polsky-Cynkin, et al. "Use of DNA Immobilized on Plastic and Agarose Supports to Detect DNA by Sandwich Hybridization"; Clinical Chemistry; 1985; pp. 1438-1443; vol. 31, No. 9.
Hudson "The Fixation and Retention of Viral and Mammalian Deoxyribonucleic Acids on Nitrocellulose Filters"; Canadian Journal of Biochemistry; 1971; pp. 631-638; vol. 49.
Innis, et al. "PCR Protocols A Guide to Methods and Applications"; 1990; pp. 119-128; Academic Press, Inc. San Diego, CA, US.
Vehls, et al. "Trends in Genetics"; TIG, Technical Tips; Oct. 1993; pp. 336-337; vol. 9, No. 10.
Reed, et al. "Rapid preparation of DNA dot blots from tissue samples, using hot alkaline lysis and filtration onto charge-modified nylon membrane"; Nucleic Acids Research; 1990; pp. 3093; vol. 18, No. 10; Oxford University Press.
David, et al. (Eds.) "Basic Methods in Molecular Biology"; Elsevier Science Publishing Co.; 1986; pp. 42-78 and 130-149; New York, NY.

* cited by examiner

Primary Examiner—Ethan Whisenant
(74) Attorney, Agent, or Firm—Hogan & Hartson LLP

(57) ABSTRACT

This invention is directed to a process for tightly binding nucleic acid to solid phase and corresponding processes for the utilization thereof. Nucleic acid is bound to solid phase matrices exhibiting sufficient hydrophilicity and electropositivity to tightly bind the nucleic acids from a sample. These processes include nucleic acid (double or single stranded DNA and RNA) capture from high volume and/or low concentration specimens, buffer changes, washes, and volume reductions, and enable the interface of solid phase bound nucleic acid with enzyme, hybridization or amplification strategies. The tightly bound nucleic acid may be used, for example, in repeated analyses to confirm results or test additional genes in both research and commercial applications. Further, a method is described for virus extraction, purification, and solid phase amplification from large volume plasma specimens.

19 Claims, 21 Drawing Sheets

Panel A

Panel B

| | XTRA AMP | | | Ti SLURRY | |
|---|---|---|---|---|---|
| 1 | | | 1 | | |
| 2 2 | | $10^3$ | 4 2 | | $10^3$ |
| 3 3 | | 1 | 4 3 | | 1 |
| 1 4 | | $10^2$ | 4 4 | | $10^2$ |
| 3 5 | | 1 | 4 5 | | 1 |
| 4 6 | | $10^1$ | 1 6 | | $10^1$ |
| 1 7 | | 1 | 0 7 | | 1 |
| 0 8 | | $2 \times 10^0$ | 0 8 | | $2 \times 10^0$ |
| 0 9 | | 1 | 0 9 | | 1 |
| 10 | | | 10 | | |
| 11 | | | 11 | FILTER/Ti SLURRY | |
| 012 | NC·XA | $10^3$ | 412 | | $10^3$ |
| 13 | | 1 | 413 | | 1 |
| 014 | NC·Ti | $10^2$ | 014 | | $10^2$ |
| 15 | | 1 | 315 | | 1 |
| 016 | NC·F | $10^1$ | 016 | | $10^1$ |
| 17 | | 1 | 217 | | 1 |
| 18 | *Note: All Signals Read | $2 \times 10^0$ | 218 | | $2 \times 10^0$ |
| 19 | at 20 minutes. | 1 | 019 | | 1 |

FIG. 16

SEQUENCE LISTING

<160> NUMBER OF SEQ ID NOS: 10

<210> SEQ ID NO 1
<211> LENGTH: 21
<212> TYPE: DNA
<213> ORGANISM: Cryptosporidium parvum

<400> SEQUENCE: 1
gaggatagag gcatttggtt g                                           21

<210> SEQ ID NO 2
<211> LENGTH: 20
<212> TYPE: DNA
<213> ORGANISM: Cryptosporidium parvum

<400> SEQUENCE: 2
gttttgtagg ggtcgctcat                                             20

<210> SEQ ID NO 3
<211> LENGTH: 100
<212> TYPE: DNA
<213> ORGANISM: Cryptosporidium parvum

<400> SEQUENCE: 3
ctatatcgta atacgctctg attacgtagg gagtggtact cctaacagta ggcctctgat    60
ttgtcagtcg acataccgct gcgctcaaat ccttttagaa                         100

<210> SEQ ID NO 4
<211> LENGTH: 15
<212> TYPE: DNA
<213> ORGANISM: Mycobacterium tuberculosis

```
<400> SEQUENCE: 4
cgatcgagca agcca                                                        15

<210> SEQ ID NO 5
<211> LENGTH: 15
<212> TYPE: DNA
      AB5428 I1 D2 US.ST25.txt
<213> ORGANISM: Mycobacterium tuberculosis

<400> SEQUENCE: 5
cgagccgctc gctga                                                        15

<210> SEQ ID NO 6
<211> LENGTH: 40
<212> TYPE: DNA
<213> ORGANISM: Artificial
<220> FEATURE:
<223> OTHER INFORMATION: primer

<400> SEQUENCE: 6
accgcatcga atgcatgtct cgggtaaggc gtactcgacc                              40

<210> SEQ ID NO 7
<211> LENGTH: 40
<212> TYPE: DNA
<213> ORGANISM: Artificial
<220> FEATURE:
<223> OTHER INFORMATION: primer

<400> SEQUENCE: 7
cgattccgct ccagacttct cgggtgtact gagatcccct                              40

<210> SEQ ID NO 8
<211> LENGTH: 28
<212> TYPE: DNA
<213> ORGANISM: Homo sapiens

<400> SEQUENCE: 8
ataatccacc tatcccagta ggagaaat                                           28

<210> SEQ ID NO 9
<211> LENGTH: 28
<212> TYPE: DNA
<213> ORGANISM: Homo sapiens

<400> SEQUENCE: 9
tttggtcctt gtcttatgtc cagaatgc                                           28

<210> SEQ ID NO 10
<211> LENGTH: 100
<212> TYPE: DNA
<213> ORGANISM: Homo sapiens

<400> SEQUENCE: 10
atcctatttg ttcctgaagg gtactagtag ttcctgctat gtcacttccc cttggttctc        60
tcatctggcc tggtgcaata ggccctgcat gcactggatg                             100
```

NUCLEIC ACID ARCHIVING

RELATED APPLICATIONS

This application is a Divisional of U.S. patent application Ser. No. 10/690,359 filed Oct. 21, 2003 now U.S. Pat. No. 7,087,387, which is a Divisional of U.S. patent application Ser. No. 09/944,604 filed Aug. 31, 2001, (now U.S. Pat. No. 6,872,527), which is a Continuation-In-Part of U.S. patent application Ser. No. 09/061,757 filed Apr. 16, 1998, (now U.S. Pat. No. 6,291,166), which claims priority to U.S. Provisional Patent Application Ser. No. 60/041,999 filed Apr. 16, 1997, all of which are incorporated herein in their entireties by this reference.

FIELD OF INVENTION

This invention relates to the general fields of molecular biology, biochemistry, genetics, and biological research. More specifically, the invention relates to methods for capturing and tightly binding nucleic acid from any biological specimen onto a solid phase matrix. The solid phase-bound nucleic acid can be directly utilized multiple times as an accessible substrate for a number of manipulations including solid phase nucleic acid enzyme reactions, oligonucleotide or probe hybridization, and/or signal or target amplification reactions. This invention further relates to commercial applications interfacing nucleic acid capture with nucleic acid hybridization and/or amplification.

BACKGROUND AND PRIOR ART

The molecular structure of nucleic acids provides for specific detection by means of complementary base pairing of oligonucleotide probes or primers to sequences that are unique to specific target organisms or tissues. Since all biological organisms or specimens contain nucleic acid of specific and defined sequences, a universal strategy for nucleic acid detection has extremely broad applications in a number of diverse research and development areas as well as commercial industries. The potential for practical uses of nucleic acid detection was greatly enhanced by the description of methods to amplify or copy, with fidelity, precise sequences of nucleic acid found at low concentration to much higher copy numbers, so that they are more readily observed by detection methods.

The original nucleic acid amplification method is the polymerase chain reaction (PCR) described by Mullis et al. (U.S. Pat. Nos. 4,683,195, 4,683,202, and 4,965,188, all of which are specifically incorporated herein by reference). Subsequent to the introduction of PCR, a wide array of strategies for amplification have been described, such as nucleic acid sequence based amplification (NASBA) (U.S. Pat. No. 5,130,238 to Malek), isothermal methodology (U.S. Pat. No. 5,354,668 to Auerbach), ligase chain reaction (U.S. Pat. No. 5,427,930 to Buirkenmeyer), and strand displacement amplification (SDA), (U.S. Pat. No. 5,455,166 to Walker), all of which are specifically incorporated herein by reference. Some of these amplification strategies, such as SDA or NASBA, require a single stranded nucleic acid target. The target is commonly rendered single stranded via a melting procedure using high temperature prior to amplification.

Prior to nucleic acid amplification and detection, the target nucleic acid must be extracted and purified from the biological specimen such that inhibitors of amplification reaction enzymes are removed. Further, a nucleic acid target that is freely and consistently available for primer annealing must be provided. Numerous strategies for nucleic acid purification are known. These include, for example, phenol-chloroform and/or ethanol precipitation (Sambrook et al., *Molecular Cloning: A Laboratory Manual*, 2nd Ed., Cold Spring Harbor Laboratory, Cold Spring Harbor, N.Y. (1989)), high salt precipitation (Dykes, *Electrophoresis* 9:359-368 (1988)), proteinase K digestion (Grimberg et al., *Nucleic Acids Res.*, 22:8390 (1989)), chelex and other boiling methods (Walsh et al., *Bio/techniques* 10:506-513 (1991)) and solid phase binding and elution (Vogelstein and Gillespie, *Proc. Nat. Acad. Sci. USA*, 76:615-619 (1979)), all of which are specifically incorporated herein by reference.

The analysis of nucleic acid targets therefore consists of three steps: nucleic acid extraction/purification from biological specimens, direct probe hybridization and/or amplification of the specific target sequence, and specific detection thereof. In conventional protocols each of these three steps is performed separately, thus making nucleic acid analysis labor intensive. Further, numerous manipulations, instruments and reagents are necessary to perform each step of the analysis. Another concern with current methodologies is the significant chance of specimen cross-contamination, for example, between concurrently run specimens or from a previously amplified sample.

For analysis purposes, nucleic acid must frequently be extracted from extremely small specimens from which it is difficult, if not impossible, to obtain a second confirmatory specimen. Examples include analysis of crime scene evidence or fine needle biopsies for clinical testing. In such examples, the extent of the genetic testing and confirmation through replica testing is thus limited by the nucleic acid specimen size. Using conventional extraction protocols for these small specimens, the nucleic acid is often lost or yields are such that only a single or few amplification analyses are possible.

The requirements for binding of DNA to solid phases and subsequently being able to elute the DNA therefrom have been described by Boom (U.S. Pat. No. 5,234,809, which is specifically incorporated herein by reference) and Woodard U.S. Pat. Nos. 5,405,951, 5,438,129, 5,438,127, all of which are specifically incorporated herein by reference). Specifically, DNA binds to solid phases that are electropositive and hydrophilic. Electropositive elements can be rendered sufficiently hydrophilic by hydroxyl (—OH) or other groups, resulting in a solid phase matrix that tightly binds DNA, while proteins or inhibitors do not bind to the solid phase matrix. Since conventional purification methods require elution of the bound nucleic acid, solid phase matrices that bind nucleic acids but do not allow substantially complete elution have been described as being of no use for DNA purification. In fact, considerable effort has been expended to derive solid phase matrices sufficiently hydrophilic to adequately bind nucleic acid and yet allow for its elution therefrom (See, e.g., U.S. Pat. Nos. 5,523,392, 5,525,319 and 5,503,816, all to Woodard and incorporated herein by reference).

Boom, supra, describes solid phase DNA amplification using high chaotropic salt to reversibly bind the DNA to silica. However, when the silica-bound DNA is placed in the amplification reaction buffer, the nucleic acid is actually eluted from the silica. Therefore, the amplification according to the method of Boom actually occurs in solution, not on solid phase. Furthermore, since the nucleic acid is eluted from the solid phase prior to amplification, the amplification can only be performed once.

Del Rio et al., *Bio/techniques* 20:970-974 (1996)) describe filter entrapment of nucleic acid in a manner allowing for repeat amplification. However, they do not describe a binding mechanism that is irreversible, and therefore the method is only recommended for analysis of higher nucleic acid concentrations, and then only for a limited number of analyses.

It would be advantageous to directly integrate nucleic acid purification and/or extraction with other nucleic acid analyses and/or manipulations so as to simplify the analysis procedure and methodologies, as well as reduce and/or remove the risk of cross-contamination. It further would be advantageous to eliminate the melt step necessary for generating single strand nucleic acid for probe hybridization or amplification primer annealing.

SUMMARY OF THE INVENTION

Accordingly, this invention provides methods for directly interfacing nucleic acid purification and/or extraction with other methodologies for nucleic acid analyses and/or manipulations.

This invention further provides methods for direct solid phase nucleic acid manipulation and/or analysis, wherein the manipulation and/or analysis is performed without elution of the nucleic acid from the solid phase. This invention comprises the use of solid phase materials comprising one or more highly electropositive elements which have been rendered hydrophilic, so as to result in solid phase materials having high affinity for nucleic acids.

This invention further provides methods for extracting and tightly binding nucleic acid from specimens, and thus permanently archiving the nucleic acid.

The methods of this invention allow for repeated analyses and/or manipulations of the matrix-bound nucleic acid, wherein the bound nucleic acid is neither altered nor exhausted during analysis.

This invention further provides methods for capturing and tightly binding nucleic acid at low concentrations and at high flow rates from any biological specimen.

This invention further provides a novel mechanism for converting double stranded nucleic acid to single stranded nucleic acid without any melting step.

Accordingly, one embodiment of this invention provides a method that uses solid phase matrices to tightly bind nucleic acid for direct solid phase manipulation and analyses including, but not limited to, enzyme recognition, hybridization, and primer dependent amplification, wherein the nucleic acid is not washed off of the solid phase matrix during repeated manipulations and analyses.

This invention further provides methods of coating surfaces of various substrates with a solid phase matrix of this invention, and uses thereof.

This invention further provides kits for nucleic acid analysis or manipulation, comprising at least one container comprising a substrate having a solid phase matrix coated on its surface.

Other features and advantages of the instant invention will become apparent from the following detailed description which, taken in conjunction with the accompanying figures, illustrates by way of example, the principles of the instant invention.

BRIEF DESCRIPTION OF THE FIGURES

FIG. 16 shows lateral flow strips with prominent bands obtained by NASBA amplification of RNA from *Escherichia coli* dilutions using either Xtra Amp™ tubes or a $Ti_2O_3$ slurry as the solid phase matrix.

DETAILED DESCRIPTION OF THE PREFERRED EMBODIMENT

Figure 1:
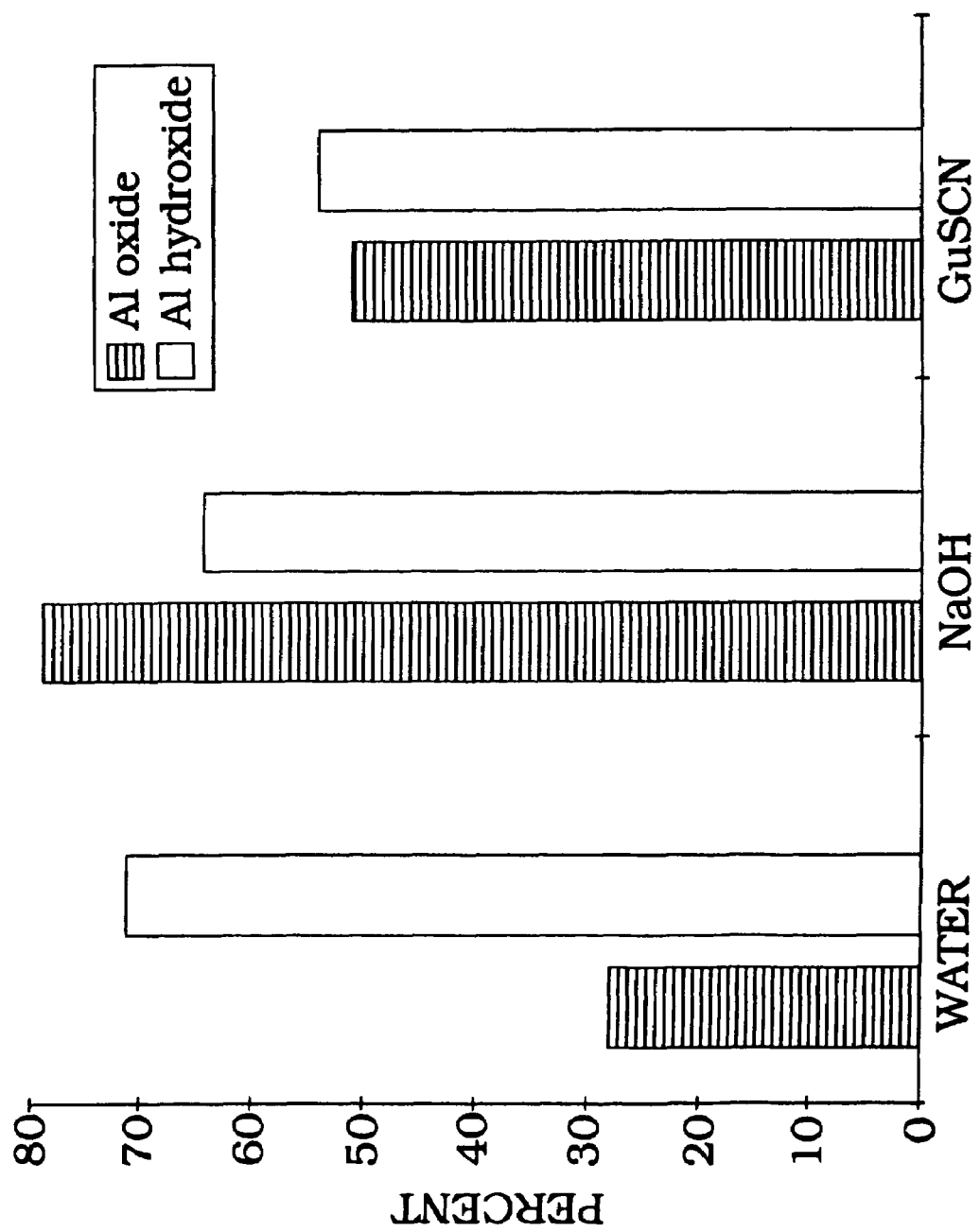
FIG. 1 is a bar graph illustrating the percentage binding of $^{32}P$ radiolabeled DNA to either aluminum oxide or aluminum hydroxide following one hour room temperature incubation with rotation in water, 0.1 N sodium hydroxide (NaOH), or 4 M guanidine thiocyanate (GuSCN) binding buffers.

It is understood that both the foregoing general description and the following detailed description are exemplary and explanatory only and are not restrictive of the invention as claimed.

This invention is based on novel methods of tightly binding RNA, DNA or other nucleic acids to a solid phase matrix, and to uses of the matrix-bound nucleic acids. The methods described herein provide for long term storage of nucleic acid and/or repeat analysis and/or expanded analysis and/or multiple manipulations of the bound nucleic acid directly on the solid phase matrix without eluting the nucleic acid from the matrix. Each of the methodologies disclosed herein overcomes the drawbacks of the prior art.

Certain embodiments of this invention provide specific applications of nucleic acids that have been tightly bound to solid phase materials. These known materials have previously been considered by the skilled artisan to be incompatible with nucleic acid analysis and/or manipulation since the nucleic acid cannot be eluted from the solid phase materials. Furthermore, in contrast to conventional methods, the nucleic acid manipulations in certain embodiments of this invention occur while the nucleic acid is still bound to the solid phase matrix.

More specifically, this invention comprises the use of solid phase matrices comprising one or more highly electropositive elements that have been rendered hydrophilic, for example, by hydroxyl (OH) groups or other groups, so as to result in a solid phase matrix having high affinity for nucleic acids. As used herein, the term "electropositive" refers to any element or material that attracts electrons. Examples of electropositive materials suitable for purposes of this invention include, but are not limited to, materials generally containing one or more elements selected from the group consisting of aluminum, titanium, zirconium, hafnium, scandium, yttrium, lanthanum, vanadium, tantalum, chromium, molybdenum, tungsten, boron, gallium, indium, germanium, tin, and lead.

Solid phase matrices suitable for purposes of this invention include, but are not limited to, oxides of the above-described electropositive materials. Examples include aluminum oxides including, but not limited to, alpha aluminum oxide (α-$Al_2O_3$), gamma aluminum oxide (γ-$Al_2O_3$), and thin films of aluminum oxide of mixed compositions ($Al_xO_y$). As used herein, the term "mixed composition" refers to compositions comprising metal oxides of various compositions which can be represented by the formula $M_xO_y$, where the subscripts "x" and "y" indicate the elemental composition of the compound, and "x" and "y" can be integers or fractions. For example, an aluminum oxide of mixed composition comprises mixtures of aluminum oxides having the formula $Al_xO_y$. Additional examples of suitable matrices include titanium oxide ($Ti_2O_3$), and modified zirconium oxide ($ZrO_2$). As used herein, the term "modified zirconium oxide" refers to zirconium oxide which has been exposed to an acid such as hydrochloric acid or nitric acid, or a base such as potassium hydroxide, resulting in a hydrolyzed surface composition.

The solid phase matrices of this invention have high affinities for nucleic acids. Therefore, nucleic acids that are contacted with a solid phase matrix of this invention under appropriate conditions become tightly bound to the matrix. As used herein, the term "tightly bound" means that the nucleic acid is sufficiently bound to the solid phase matrix such that the majority of the nucleic acid remains bound to the matrix during manipulations and/or analyses of the bound nucleic acid. That is, only a minor amount of the matrix-bound nucleic acid is displaced from the solid phase matrix under certain buffer conditions during the manipulations and/or analyses.

This invention exploits the irreversible binding of nucleic acid to these solid phase matrices for specific applications. The tightly bound nucleic acid can be directly brought into contact with reaction mixtures that provide for nucleic acid manipulation and/or analyses as discussed below in detail and in the Examples which follow.

In one embodiment, this invention provides for repeat and/or expanded analysis of the bound nucleic acid following its capture onto the solid phase matrix (nucleic acid archiving). The tightly bound nucleic acid described herein is stable at ambient room temperature, perhaps indefinitely.

Thus, this invention provides a useful method of nucleic acid storage. The stored nucleic acid can then be analyzed or manipulated at a later point in time when needed. This is extremely useful in applications where a biological specimen is found in limited quantity and/or might be irreplaceable and where the reanalysis, either immediately or after storage of the original specimen, can be beneficial. Areas where this occurs include, for example, forensics, medical and biological research, veterinary or human clinical diagnostics, dentistry, environmental, food, or water microbiology, and agricultural or other industrial applications.

In another embodiment, this invention provides for a method of exclusively binding either DNA or RNA to a solid phase matrix from a sample containing both DNA and RNA. For example, one method for archiving nucleic acid comprising contacting a sample containing both DNA and RNA with a solid phase matrix under conditions wherein the matrix exclusively binds DNA. In this embodiment, such conditions comprise adding either to the sample or the matrix a buffer selected from the group consisting of guanidine thiocyanate-based buffers, alkaline buffers, lithium chloride, and detergent based buffers including, but not limited to, sodium dodecyl sulfate (SDS), Tween 20, Triton X-100, NP-40, N-lauroylsarcosine, and other common detergents, prior to contacting said sample with the solid phase matrix.

Alternatively, this invention also provides a method for archiving nucleic acid comprising contacting a sample containing both DNA and RNA with a solid phase matrix under conditions wherein the matrix exclusively binds RNA. In this embodiment, such conditions comprise adding a DNA degrading reagent, for example a DNA degrading enzyme such as DNase, to the sample in the presence of a buffer to lyse the cells and simultaneously degrade the DNA.

In another embodiment, the tightly bound nucleic acid allows for stringent aqueous washes, buffer changes and volume reductions during procedural manipulations of the bound nucleic acid. That is, the solid phase matrix sufficiently binds the nucleic acid such that the majority of the nucleic acid remains tightly bound to the matrix even after multiple washes with aqueous buffers. Thus, this invention provides a convenient mechanism for buffer changes and volume reduction.

In another embodiment, this invention provides novel methods for rapid DNA and RNA capture that directly interface nucleic acid extraction and purification with nucleic acid hybridization and/or nucleic acid amplification. The extractions can be performed manually or automated. As used herein, "nucleic acid hybridization" includes, but is not limited to, (a) hybridization of a matrix-bound nucleic acid probe with a target nucleic acid present in a sample, (b) hybridization of a matrix-bound target nucleic acid with a primer nucleic acid, and (c) hybridization of a matrix-bound target nucleic acid with a probe nucleic acid.

For example, one embodiment of this invention comprises a method of amplifying one or more target nucleic acids, comprising (a) contacting a sample containing one or more target nucleic acids with a solid phase matrix of this invention and a buffer that allows the target nucleic acid sequence(s) to become tightly bound to the matrix as single stranded nucleic acid; (b) contacting the matrix-bound target nucleic acid with a set of primer nucleic acid sequences and a buffer, thereby allowing the primer set to hybridize to the matrix-bound target nucleic acid; and (c) amplifying the target nucleic acid(s) to produce an amplified reaction mixture, wherein the target nucleic acid sequence remains tightly bound to the matrix.

In one embodiment of solid phase amplification, a buffer is employed that allows the target nucleic acid sequence(s) to become tightly bound to the matrix. Examples of such buffers include, but are not limited to, guanidine thiocyanate-based buffers, alkaline buffers, lithium chloride, and detergent based buffers including, but not limited to, Triton X-100, NP-40, NP-lauroylsarcosine, sodium dodecyl sulfate (SDS), Tween 20, and other common detergents. In addition, phosphate buffers have been identified that reduce binding of the primer sequences to the solid phase matrix and the subsequent loss in efficiency.

In another embodiment, two or more different nucleic acid targets are bound to the solid phase matrix, and the target nucleic acids are amplified in series.

When employing a high affinity solid phase matrix according to the methods of this invention for capturing double-stranded DNA, the nucleic acid may be captured as double stranded nucleic acid directly from aqueous biological specimens or buffers. Alternatively, in some cases it is necessary to bind the DNA to the solid phase matrix as single-stranded DNA. Accordingly, this invention includes methods of modifying buffer conditions to allow double-stranded DNA to be bound to the matrix as single-stranded DNA, as described below in detail.

For example, binding nucleic acid as a single strand is necessary in order to interface with hybridization and/or isothermal amplification methods. Thus, when the target nucleic acid is double-stranded DNA, the sample is adjusted to an alkaline pH or a high chaotropic salt concentration to allow the double-stranded nucleic acid to become bound to the solid phase matrix as single-stranded nucleic acid.

Various nucleic acid amplification methodologies are suitable for the direct solid phase nucleic acid amplifications of this invention. Such methodologies include, but are not limited to, PCR, SDA, NASBA, IsoCR, CRCA, Q beta replicase, branched chain DNA, and RT-PCR. Such methodologies are well known to those skilled in the art and need not be described in further detail. In addition, an amplification method referred to as "unwinding coil amplification" (or "UNCA") may be applied to the methods of this invention. "Unwinding coil amplification" is disclosed in copending U.S. Patent Provisional Application Ser. No. 60/299,410, filed Jun. 19, 2001, and entitled "Unwinding Coil Amplification and Methods of Use Thereof," which is specifically incorporated herein by reference. Briefly, this method resembles Rolling Circle-type amplification technologies in that a long amplification product is formed from many tandem repeats of a circular template. However, it differs from Rolling Circle in that the circular template is a linear DNA which coils back upon itself and is circular only by virtue of hybridization of the two ends of the molecule with each other.

The method of this invention for amplifying a target nucleic acid sequence directly on the solid phase matrix also includes methods in which the matrix-bound sample contains multiple target nucleic acid sequences. In this method, the target nucleic acid is pre-amplified according to the method described in copending U.S. patent application Ser. No. 09/589,560 to Gerdes, et al., filed Jun. 6, 2000, entitled "Methods of Multiplexing Amplification Reactions," which is specifically incorporated herein by reference. According to the Gerdes et al. method, a two-step multiplex amplification reaction is performed, where the first step truncates the standard initial multiplex amplification round to "boost" the sample copy number by only a 100 to 1000 fold increase in the target. This step of pre-amplifying multiple target sequences is performed directly on the solid phase according to the methods of this invention. Further, the multiple target sequences are amplified simultaneously. Following the pre-amplification step, the product is divided into optimized secondary single, solid phase amplification reactions, each reaction mixture containing one of the primer sets that were used previously in the first or multiplexed booster step.

Yet another embodiment of this invention provides novel methods for direct analysis of target nucleic acid bound to the solid phase as either single or double strands. One example of this embodiment includes the determination and/or quantitation of a target nucleic acid which may be present in a sample. More specifically, another embodiment of this invention includes a method of capturing a target nucleic acid from a sample, comprising: (a) contacting a probe comprising a nucleic acid sequence that is complementary to a specific sequence of the target nucleic acid with a solid phase matrix under conditions that allow the probe to become tightly bound to the solid phase matrix; and (b) contacting the matrix-bound probe with the sample under conditions that allow the target nucleic acid to hybridize to the matrix-bound probe, whereby the target nucleic acid is captured by the probe. In this capture method, phosphate buffers may be utilized which reduce binding of the target nucleic acid to the solid phase matrix but which allow the target nucleic acid to bind to the matrix-bound probe.

The hybridized target can then be detected and/or quantitated according to methods well known to those skilled in the art. After detection and/or quantitation, the complex can be dissociated and the matrix washed to remove the target nucleic acid. The nucleic acid probe remains tightly bound to the matrix during all of the above manipulations, and therefore can be reused multiple times. This methodology is particularly well suited for applications such as microarrays, lab-on-a-chip systems, and automated robotics.

Specimens that contain high levels of endogenous or background nucleic acid such as blood are extremely difficult to analyze for the presence of low level specific targets. Accordingly, another embodiment of this invention provides a method that utilizes a solid phase matrix to irreversibly capture low level nucleic acids in such specimens. The method comprises changing buffer conditions such that the solid phase materials can selectively capture target sequences even in the presence of high levels of background nucleic acid. The embodiment of probe hybridization therefore provides high stringency for commercial applications such as microarray hybridizations that demand low background in order to attain high sensitivity.

In yet another embodiment, this invention allows for gravity or high flow rate solid phase chromatography as a means of either capturing and/or concentrating nucleic acid from large volume specimens or removing contaminant nucleic acid from aqueous buffers or solutions. More specifically, one embodiment of this invention provides methods for capturing and tightly binding nucleic acid, at low concentrations and at high flow rates, from any sample by flowing the sample onto or over a solid phase matrix of this invention. In this manner, the nucleic acid becomes tightly bound to and concentrated on the matrix, while undesired components in the sample are washed off the matrix. In one embodiment, the sample is flowed over the matrix at a rate between about 0.5 mL/min and 2 mL/min. The bound nucleic acid can be washed extensively with aqueous buffers without elution from the solid phase to provide a purified nucleic acid.

The binding properties of RNA to a high affinity solid phase matrix have not been previously studied in the art. Another aspect of this invention demonstrates that RNA is tightly bound by the solid phase matrices described herein. This invention further provides methods of amplifying the matrix-bound RNA and the stable storage of the matrix-bound RNA.

The methods of this invention are also useful for commercial applications for automating nucleic acid extraction, concentrating low copy nucleic acid from high volume specimens, and interfacing extraction and purification with amplification or hybridization nucleic acid capture. Commercial applications include high throughput nucleic acid testing that would benefit from robotic automation, or economical screening of low prevalence targets by means of pooled specimen testing.

The instant invention describes methods for immediately capturing and tightly binding nucleic acid on a solid phase matrix at high flow rates. Binding occurs for both DNA and RNA even at high volumes and/or low target concentrations. Tightly bound nucleic acid can be subjected to stringent aqueous washes, stored for later analysis, and repeatedly amplified or otherwise analyzed or manipulated without significant displacement of the nucleic acid from the solid phase matrix. Since the nucleic acid remains bound to the solid phase even after multiple buffer washes, hybridization reactions, amplification reactions, etc., the nucleic acid can be reanalyzed an unlimited number of times. Repeated solid phase manipulation of any nucleic acid may be accomplished according to the methods of present invention, as well as with other types of nucleic acid manipulations well known to those skilled in the art. The ability to reanalyze the same nucleic acid specimen according to the methods of this invention provides a means of result confirmation and/or expanded analysis.

The general principles and conditions for manipulations, including hybridization and amplification are well known in the art. Regardless of the specific application of the instant invention, the methodology details are calculated according to protocols well known in the art as well as those disclosed herein. Further, the refinements of these necessary calculations are routinely made by those of ordinary skill in the art without undue experimentation.

One skilled in the art will recognize that tight binding of nucleic acid onto a solid phase matrix, as disclosed herein, may be performed with a broad range of samples. Such samples include, but are not limited to, biological samples derived from agriculture sources, bacterial and viral sources, and from human or other animal sources, as well as other samples such as waste or drinking water, agricultural products, processed foodstuff and air. More specifically, samples include, for example, blood, stool, sputum, mucus, cervical or vaginal specimens, cerebral spinal fluid, serum, urine, saliva, teardrop, biopsy samples, histological tissue samples, tissue culture products, bacterial cultures, agricultural products, environmental samples, waste or drinking water, foodstuff and air. The present invention is useful for the irreversible binding of nucleic acid to a solid phase matrix from any sample containing nucleic acid, either naturally occurring or as a contaminant.

This invention further comprises methods of coating surfaces of substrates with the solid phase matrices of this invention. Such substrates include polymers (e.g., plastics) and oxide materials such as glass. These substrates can be of any shape suitable for nucleic acid archiving, analysis, and/or manipulations, including, but not limited to, tubes, plates, membranes, capillaries, slides, beads, microparticles, fibers, microchannels, and microarrays. Accordingly, any of the above-described methods of nucleic acid archiving and direct solid phase analysis and/or manipulation can be carried out using the coated surfaces and substrates prepared as described herein.

One method for coating polymer substrates such as standard PCR tubes with a solid phase matrix involves using adhesives. However, adhesives can be inhibitory to amplification reactions, especially in assays where detecting low copy number is necessary. Accordingly, this invention provides improved methods for attaching solid phase matrix to polymers or plastic surfaces in a manner that eliminates the amplification inhibitors that can be present in adhesives. The plastic surfaces include any surface formed from polymers and include tubes, plates, membranes, beads, microparticles, microchannels, microarrays, and any other suitable format fabricated from polymers. Methods of this invention for coating polymer substrates are described in detail in Example 13.

In addition to the above-described polymers, this invention further provides methods of coating glass (silicon dioxide) or other oxide substrates, such as aluminum oxide or titanium dioxide, with a solid phase matrix described herein. Any format of a glass or oxide substrate is suitable for use in nucleic acid manipulations. Examples include, but are not limited to, glass capillaries, glass fiber filters, microscope slides, porous glass wool, and alumina filters. Coatings of solid phase matrices can be deposited on glass surfaces in capillaries, slides, and other formats, as well as other oxide surfaces by several methods as described in detail in Example 14.

This invention further provides kits for nucleic acid archiving, analysis and/or manipulation according to this invention. The kit generally comprises a substrate such as polymers or glass coated on one or more surfaces with a solid phase matrix. The substrate can be of any form suitable for nucleic acid manipulations, including but not limited to, PCR tubes, plates, beads, membranes, beads, microchannels, microarrays, and the like. A suitable solid phase matrix includes any electropositive material that has been rendered hydrophilic according to this invention, including but not limited to, aluminum oxide ($Al_2O_3$), alpha aluminum oxide, gamma aluminum oxide, thin film aluminum oxide of mixed composition ($Al_xO_y$), titanium oxide ($Ti_2O_3$), modified zirconium oxide ($ZrO_2$), and the like. The solid phase matrix can be coated on the surface of the polymers or glass according to the methods described in Example 14.

The kits may also comprise one or more containers containing reagents necessary for the nucleic acid manipulations and/or analyses. Examples of such reagents include, but are not limited to, lysis buffers, wash buffers, and lateral flow buffers.

The kits of this invention are suitable for manual procedures or integrated into automated or semi-automated processes. Different kit assemblies are suitable for high throughput robotics and analysis.

In one embodiment, the kit comprises (a) one or more PCR tubes coated on their inside surfaces with aluminum oxide, and (b) one or more containers comprising lysis and wash buffers. The kit may also contain instructions for using the kit. The kit of this embodiment provides an innovative system for nucleic acid extraction in which the nucleic acid remains bound in the extraction tube and can be directly amplified in this same tube.

Protocols have been validated for an increasing range of molecular targets and sample types, including whole blood, buffy coat, urine, cell culture, bacterial cells, mouse tails, and buccal swabs.

Various terms are used in this specification, for which it may be helpful to have definitions. These are provided herein, and should be borne in mind when these terms are used in the following examples and throughout the instant application.

As used herein, the term "archiving" refers to a method of tightly binding a nucleic acid to a solid phase matrix of this invention, followed by storage and/or manipulation of the bound nucleic acid. "Storage" encompasses both the capacity for delayed analysis and for repeated analysis of the same nucleic acid, as well as expanded analysis of multiple nucleic acid targets, either simultaneously or in series. For this, procedural manipulations include, but are not limited to, solid phase nucleic acid enzyme reactions, oligonucleotide or probe hybridization, and/or nucleic acid amplification reactions.

As used in this invention, a "template-dependent process" is defined as a process that involves either template-dependent recognition via a specific probe, copying procedure via signal amplification reaction, or target expansion via template dependent extension of a primer molecule. A template-dependent extension refers to nucleic acid synthesis and copy expansion of RNA or DNA target sequences, wherein the sequence of the newly synthesized strand of nucleic acid is dictated by the rules of complementary base pairing of the target nucleic acid and the primers. A template dependent process based upon complementary base pairing specifically using oligonucleotides or probes of specific sequence is known as "hybridization" detection.

A "primer" molecule refers to a nucleic acid sequence, complementary to a known portion of the target sequence/ control sequence, necessary to initiate synthesis by DNA or other polymerases, RNA polymerases, reverse transcriptases, or other nucleic acid dependent enzymes.

"Target nucleic acid sequence" or "target nucleic acid" or "target" refers to the nucleic acid that is to be captured, detected, amplified, manipulated and/or analyzed. The target nucleic acid can be present in a purified, partially purified or unpurified state in the sample.

"Nucleic acid" refers to a polymer of two or more modified and/or unmodified deoxyribonucleotides or ribonucleotides, either in the form of a separate fragment or as a component of a larger construction. Examples of polynucleotides include, but are not limited to, DNA, RNA, or DNA analogs such as PNA (peptide nucleic acid), and any chemical modifications thereof. The DNA may be a single- or double-stranded DNA, cDNA, or a DNA amplified by any amplification technique. The RNA may be mRNA, rRNA, tRNA, a ribozyme, or any RNA polymer.

In one embodiment, the term "capture" refers to the direct binding of nucleic acid onto a solid phase matrix. Binding can be direct in appropriate buffers based on the chemical and/or physical properties of nucleic acid. Alternatively, the term "capture" refers to the hybridization of a target nucleic acid present in a sample to a matrix-bound nucleic acid probe.

The present invention is directed to binding of DNA and RNA to materials that tightly bind nucleic acids, and various uses for solid phase bound DNA and RNA. This includes methods for using aluminum oxide or other materials that tightly bind nucleic acid for solid phase capture. The methods directly interface solid phase capture with various manipulations which include using aqueous buffers, single amplification or hybridization based reactions, and in-series multiplex amplification or hybridization based reactions. Further, nucleic acid capture is useful for the purpose of either removing contaminant nucleic acid, or concentrating low copy nucleic acid for the purpose of detection in either high volume or pooled specimen analysis. Aluminum oxide shows sufficient avidity for nucleic acid to bind it even at low concentrations and at high flow rates, for example, 5 mL/min. The instant invention is, thus, useful for large volume, gravity-based or, high flow rate capture as well as the capture of nucleic acid in a manner compatible with extensive aqueous washes yielding extremely clean nucleic acid that is free from inhibitors that may interfere with amplification reactions.

The hybridization reactions disclosed herein include direct hybridization of a target nucleic acid to an oligonucleotide probe captured on a solid phase matrix, wherein the matrix may be in the form of beads or planar surfaces such as blots or microarray chips. Hybridization may also include the specific capture of a specific target sequence by first tightly binding capture probes (e.g., oligonucleotides, cDNA, cloned plasmid, transcribed or synthesized RNA, or PNA) to a solid phase matrix, followed by capturing the complementary target sequence(s) from a specimen. This is particularly useful for analyzing complex specimens having a high background level of non-specific nucleic acid. The capture bead methodology is useful for specific target sequence capture such as by utilizing poly-T oligonucleotides bound to aluminum oxide ($Al_2O_3$) to purify poly A messenger RNA. By using the appropriate capture oligonucleotide, any specific target nucleic acid can be selectively removed and concentrated from a variety of specimen types.

This invention allows enzyme recognition and specific manipulation or amplification reactions with nucleic acid tightly bound to a solid phase. This includes both target amplification reactions such as PCR, RT-PCR, SDA, NASBA, IsoCR, or CRCA, as well as signal amplification reactions such as Q beta replicase or branched chain DNA (see U.S. Pat. No. 5,594,118 to Urdea et al., which is specifically incorporated herein by reference). This invention further provides the incorporation of aluminum oxide as a binding substance adhered to the reaction surface area of standard PCR tubes, as well as a protocol for rapid nucleic acid extraction that directly and conveniently interfaces with PCR thermal cycling reactions using the same PCR tube. The PCR tubes or vessels provide a platform for automation using high throughput robotics.

Buffer systems that enable the utilization of aluminum oxide for alternative nucleic acid applications are included within the scope of this invention. Such buffer systems include, for example, guanidine thiocyanate-based buffers which may also include a specific reducing agent that disrupts extremely hardy specimens, such as *Cryptosporidium parvum*. Other buffer systems suitable for purposes of this invention include alkaline buffers such as NaOH that provide a rapid and economical DNA binding buffer. In NaOH buffer, RNA is destroyed. Therefore, the use of a NaOH buffer provides a means of selectively binding only DNA. Yet another system suitable for purposes of this invention includes buffers such as phosphate buffers that reduce binding of nucleic acid to aluminum oxide. These buffer systems provides for low background signal-to-noise for sensitive and efficient microarray, bead and blot hybridizations.

The tight binding characteristics of the solid phase matrices of this invention provide for repeated analysis of either the same or different genes in series. This includes the analysis of both DNA and RNA simultaneously, or DNA and RNA independently but in series. By binding multiple probes, the hybridization capture can also be multiplexed for specific targets. Thus, the instant invention is useful for repeat or in-series analysis of any nucleic acid by either hybridization or amplification reactions. Once tightly bound, nucleic acid is stable and can be stored for prolonged periods at room temperature, refrigerated, or frozen.

Those skilled in the art readily recognize the present invention is broadly applicable to nucleic acid extraction, purification and detection. The following examples serve to explain and illustrate the present invention and therefore are not to be construed as limiting of the invention in anyway. Various modifications are possible within the scope of the invention.

EXAMPLE 1

Methods and Materials

DNA binding is measured utilizing $^{32}P$ radiolabeling. The 4361 base pair PBR322 plasmid, obtained from New England Biolabs is randomly prime labeled using the Prime-It II Stratagene kit. The plasmid is cut with Hind III, unlabeled nucleotides are removed utilizing BioRad Biospin 6, and the concentration is adjusted to one nanogram per microliter (ng/μL). Higher DNA concentrations are adjusted by the addition of salmon sperm DNA. The data for radiolabeling experiments represent the mean value of five replica data points.

Aluminum oxide beads (74-149 μm size) obtained from Aldrich (catalog No. 34,265-3) are treated with 0.1 N NaOH for 1 hour at room temperature to produce aluminum hydroxide beads. DNA binding buffers consisting of water (ddH2O), 0.1 N NaOH, or a 4 M guanidine thiocyanate buffer (12 g GuSCN, 277 μL Triton™ X-100, 2.2 ml 0.2 M EDTA pH 8.0, and 10 ml 0.1 M Tris-HCl pH 6.4) are used. Binding is permitted either by rotation in a closed microfuge tube or by gravity flow filtration. Large beads readily settle to the bottom of the tube without centrifugation and therefore facilitate washing. For gravity flow experiments a Spectrum SpectraMesh 43 μm filter (Spectrum, catalog No. 146530) is pressure fit into an ANSYS 4 mM chromatography column. The aluminum hydroxide beads are packed into this column as a liquid slurry, allowed to drain, blotted dry, washed once with 1 ml of 70% EtOH and dried prior to adding the DNA in the various binding buffers.

Xtra Bind™ (Xtrana, Inc., Broomfield, Colo.) is an alpha-alumina oxide (α-$Al_2O_3$) solid phase matrix. Xtra Amp™ (Xtrana, Inc., Broomfield, Colo.) is a PCR tube having a coating of Xtra Bind™ on the surface of the interior walls.

By way of illustration of solid phase amplification, published sequences and methods for well characterized loci are used. Sequences employed in the certain experimental procedures described below are listed in Table 1 (SEQ ID NOS: 1-10). Specifically, for PCR of HIV, the SK38/SK39 primer set (SEQ ID NOS. 8-9; Kellog and Kwok, In PCR Protocols: A Guide to Methods and Applications, M A Innis et al., eds., Academic Press Inc., pp. 337-347 (1990), which is specifically incorporated herein by reference), the control HIV DNA plasmid obtained from Perkin Elmer (catalog No. N808-0016) and rtTH reverse transcriptase amplification were used. Strand displacement amplification utilized the mycobacterium plasmid target and primer sets described by Walker, et al., *Clinical Chemistry*, 42:9-13 (1996), specifically incorporated herein by reference (SEQ ID NOS: 4-7). The human Short Tandem Repeat (STR) primer sets and protocols are the commercially available CTT and FFV multiplexes from Promega.

TABLE 1

| ID | SEQUENCE | SEQ ID NO: |
|---|---|---|
| CPSR805F | GAGGATAGAGGCATTTGGTTG | 1 |
| CPSR948R | GTTTTGTAGGGGTCGCTCAT | 2 |
| CPSR100cap | CTATATCGTAATACGCTCTGATTACGTAGGGAGTGG TACTCCTAACAGTAGGCCTCTGATTTGTCAGTCGACA TACCGCTGCGCTCAAATCCTTTTAGAA | 3 |
| B1 | CGATCGAGCAAGCCA | 4 |
| B2 | CGAGCCGCTCGCTGA | 5 |
| S1 | ACCGCATCGAATGCATGTCTCGGGTAAGGCGTACTC GACC | 6 |
| S2 | CGATTCCGCTCCAGACTTCTCGGGTGTACTGAGATCC CCT | 7 |
| SK38 | ATAATCCACCTATCCCAGTAGGAGAAAT | 8 |
| SK39 | TTTGGTCCTTGTCTTATGTCCAGAATGC | 9 |
| HIV cap | ATCCTATTTGTTCCTGAAGGGTACTAGTAGTTCCTGC TATGTCACTTCCCCTTGGTTCTCTCATCTGGCCTGGT GCAATAGGCCCTGCATGCACTGGATG | 10 |

EXAMPLE 2

Confirmation of Tight Binding of DNA to Solid Phase Matix

Figure 2:
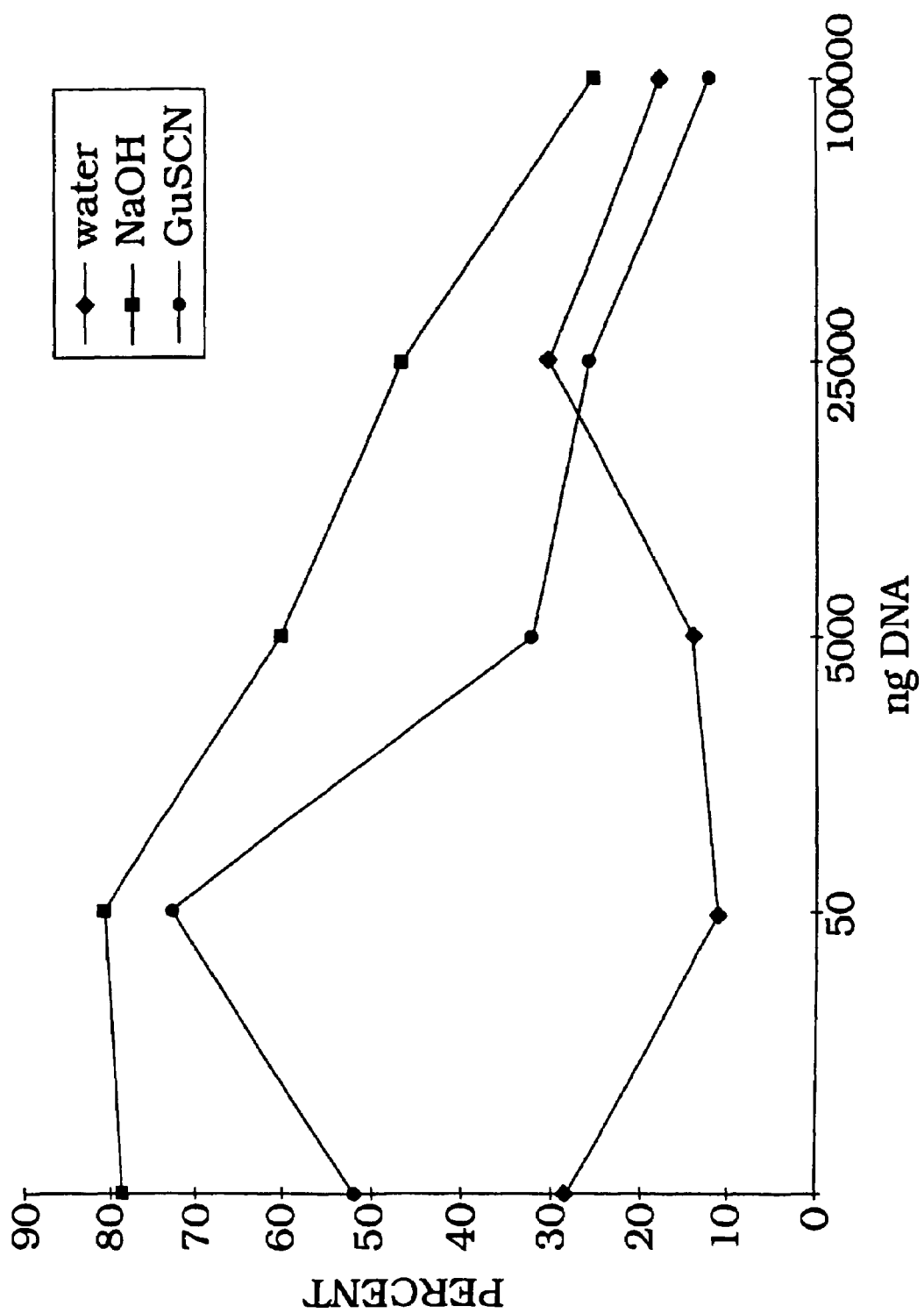
FIG. 2 is a graph illustrating the percentage of DNA bound to aluminum oxide versus the amount of DNA in nanograms (ng) following one hour room temperature incubation with rotation in either water, 0.1 N NaOH, or 4 M guanidine thiocyanate binding buffers.
Figure 3:
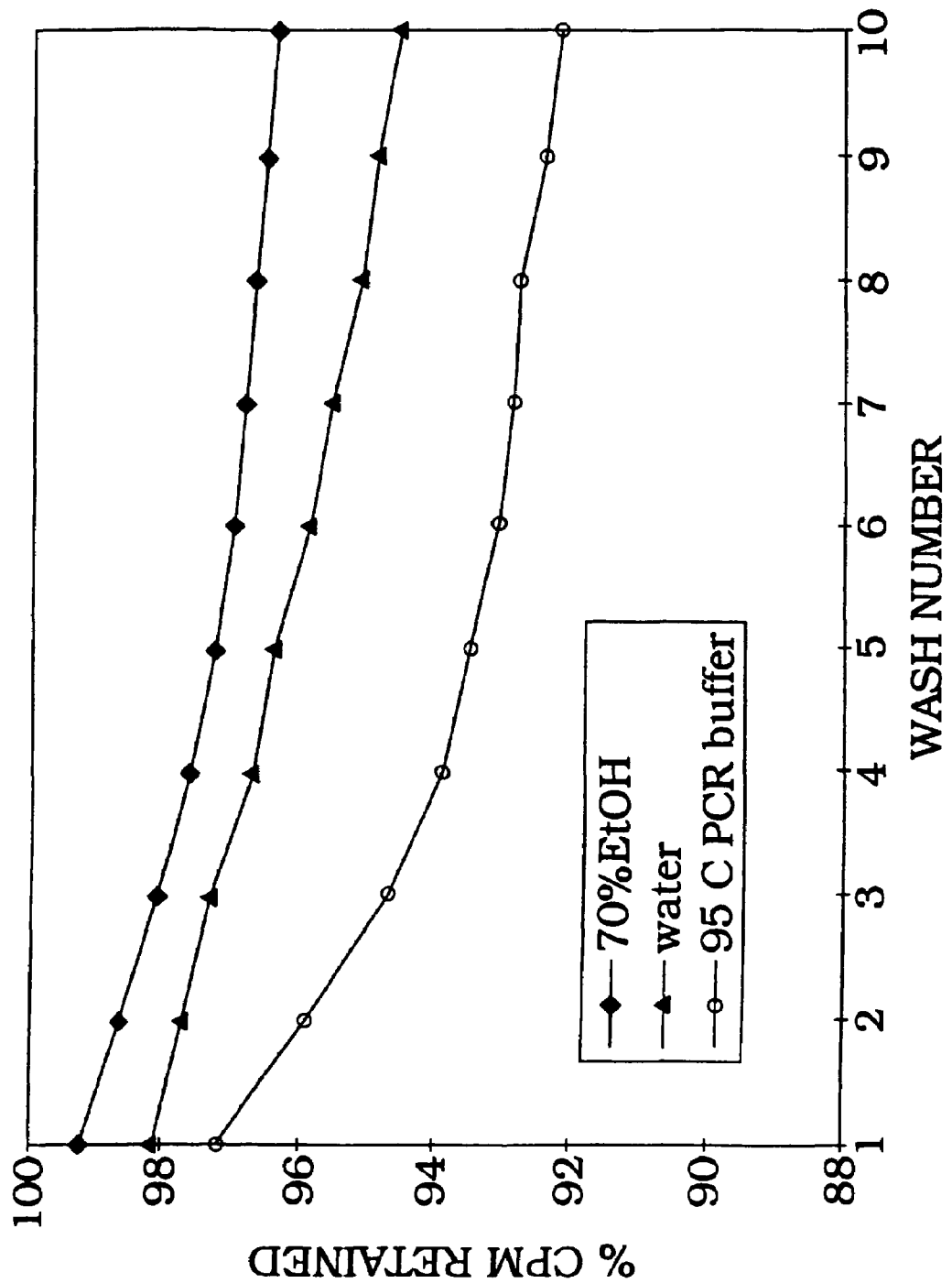
FIG. 3 is a graph illustrating the amount of radiolabeled DNA bound to aluminum oxide, shown as percent counts-per-minute (cpm) retained versus the number of times the bound DNA was washed.

Radiolabeled DNA (1 ng) is allowed to bind with aluminum oxide at room temperature, with rotation, for 1 hour in water (ddH$_2$O), 0.1 N NaOH, or 4 M guanidine thiocyanate buffer. In order to estimate binding capacity of 198 mg aluminum oxide, 1 ng of radiolabeled DNA was added to various concentrations of salmon sperm DNA (FIG. 2). As the amount of salmon sperm DNA is increased, the percent of DNA bound gradually decreases as DNA binding reaches as maximum and additional solution phase DNA cannot bind. The irreversibility of DNA binding is shown by counting the radiolabel removed following 10 sequential washes (FIG. 3). As illustrated in FIG. 3, the DNA remains tightly bound with greater than 92% retention following 10 washes with 95° C. PCR buffer. The majority of eluted counts (6%) occur during the first four washes with only a 2% total elution during the last six washes. Therefore, the data in FIG. 3 demonstrate that DNA is tightly bound to the aluminum oxide, with greater than 90% DNA retained even after 10 washes with either 70% ethanol, water or PCR buffer at 95° C. Aluminum oxide-bound DNA is, therefore, readily amenable to aqueous washes and buffer changes without centrifugation and without danger of losing the DNA. The solid phase bound nucleic acid selected from large volume samples can be washed and then resuspended at any desired volume. For example, DNA can be bound to aluminum oxide from a 3 milliliter (mL) sample containing guanidine thiocyanate buffer, washed with phosphate or Tris buffer, then the beads resuspended in small volumes of amplification reaction mixtures (50 μL). These properties provide a method of simplifying the interface between DNA purification and amplification.

EXAMPLE 3

Gravity Flow Chromatography

Figure 4:
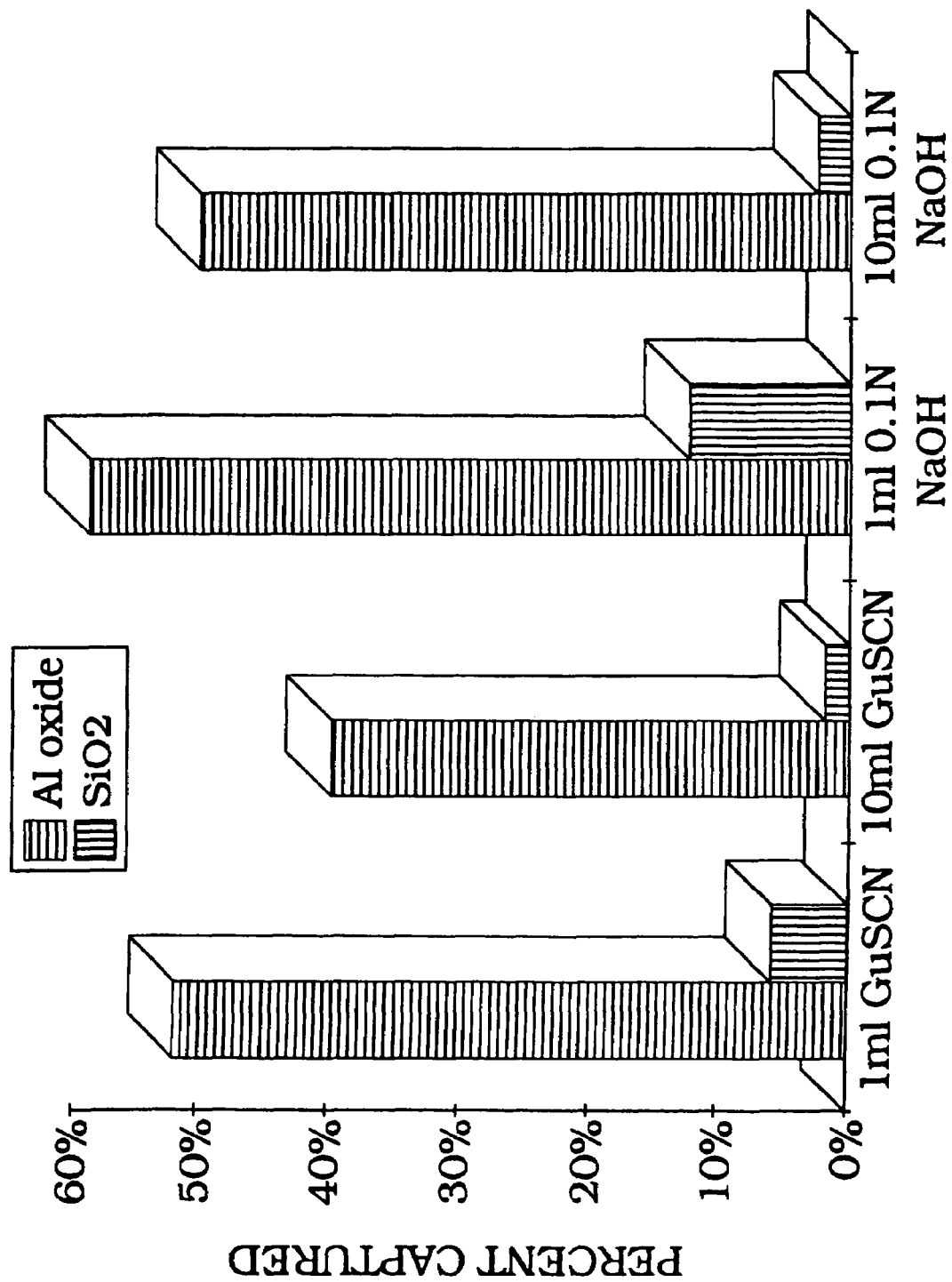
FIG. 4 is a bar graph comparing the percent DNA bound to aluminum oxide or silicon dioxide, where the DNA is diluted with either guanidine thiocyanate binding buffer or sodium hydroxide buffer.

Significant improvement in the sensitivity of DNA detection from specimens of high volume and low concentration is derived based on the capability of aluminum oxide to efficiently bind DNA at high flow rate by chromatography. Radiolabeled DNA was allowed to bind during gravity filtration of either 74-149 μm aluminum oxide beads (Al$_2$O$_3$) or 150-212 μm silicon dioxide beads (SiO$_2$) (Sigma, catalog No. GI 145). The amount of silicon dioxide or aluminum oxide was adjusted such that they both have equal surface area available for DNA binding. DNA (50 ng) bound during gravity filtration when diluted in either 1 mL guanidine thiocyanate binding buffer (1.5-2 minutes flow time, approximately 0.5 mL/min) or 10 mL guanidine thiocyanate binding buffer (5-8 minute flow times, approximately 2 mL/min). FIG. 4 compares the effect of flow rate and concentration on DNA binding to silicon dioxide versus DNA binding to aluminum oxide. Aluminum oxide was much more efficient at binding DNA during gravity flow chromatography of the 1 mL volume. The binding efficiency of silicon dioxide (SiO$_2$) in 4 M guanidine thiocyanate binding buffer was 6% versus the binding efficiency of aluminum oxide (Al$_2$O$_3$), which was 52% in the same buffer. Binding efficiency for both SiO$_2$ and Al$_2$O$_3$ improved with 1 ml NaOH binding buffer (the binding efficiency of SiO$_2$ was 12.4% versus the binding efficiency of Al$_2$O$_3$, which was 60%). Increasing the flow rate four fold by using the 10 mL volume and starting with the same 50 ng DNA (i.e., 10 times lower per mL concentration than the 1 mL specimen) drastically reduced the binding efficiency of silicon dioxide to less than 2%. In contrast, aluminum oxide suffered only a 10% reduction in total count recovery. Additional experimental procedures indicated that by repeating the chromatography using a second or third pass of the high volume specimen, up to 80% efficiency of binding is obtained for aluminum oxide (data not shown).

These results show that aluminum oxide is vastly superior for solid phase DNA binding compared to silicon dioxide and is capable of chromatographic capture of DNA at high flow rates and low concentrations. The properties of aluminum oxide thus allow for DNA concentration from pooled or large volume specimens and provide greatly increased per-milliliter sensitivity of DNA detection. The high avidity of aluminum oxide for DNA is also useful for the removal of low level DNA contaminants from water, buffers, or other reagents.

EXAMPLE 4

Solid Phase Amplification

Figure 5:
FIG. 5, panels "a" and "b", are agarose gels of $10^6$ copies of HIV DNA and a plasmid prep of mycobacterium DNAs bound to aluminum oxide in water, followed by direct solid phase amplification of the HIV DNA and mycobacterium in series. Panel "a" depicts an ethidium bromide stained agarose gel of the solid phase HIV PCR amplification product. Panel "b" depicts an ethidium bromide stained agarose gel of the solid phase mycobacterium DNA SDA amplification product.
Figure 5:
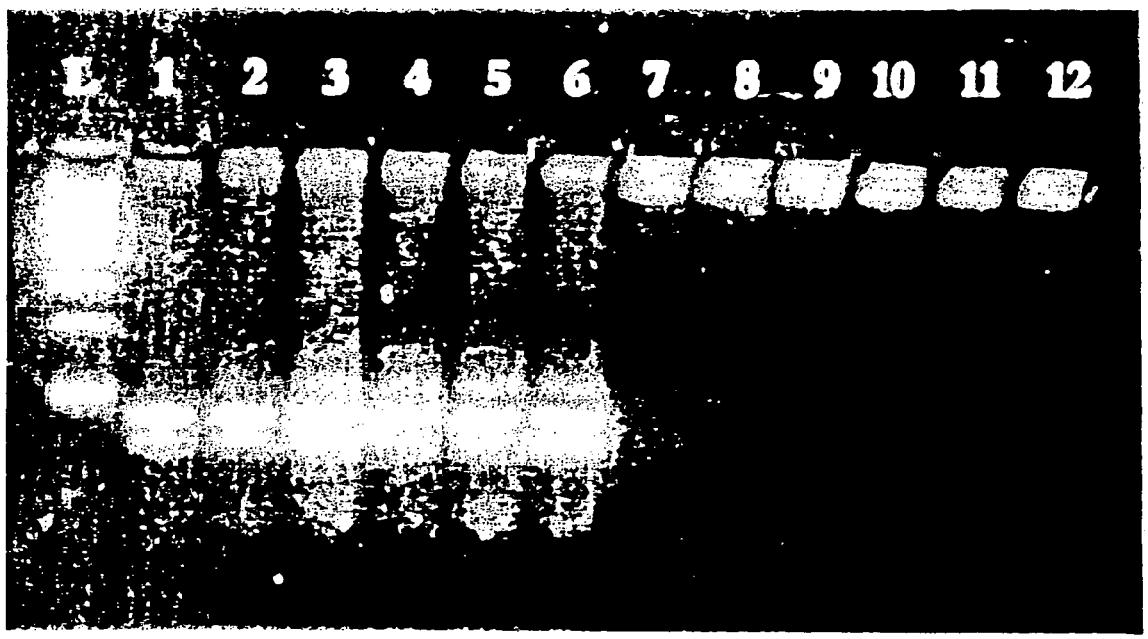

Since aluminum oxide tightly binds nucleic acid, aluminum oxide is only useful if the bound DNA can be amplified directly on the solid phase. In order to illustrate compatibility with different amplification methods, $10^6$ copies of HIV DNA and 1 µL of a plasmid prep of mycobacterium DNAs were simultaneously bound to aluminum oxide in water. These bound DNA targets were then amplified in sequence with HIV, initially amplified using 35 cycles of polymerase chain reaction (PCR) (see FIG. 5, panel "a"), followed by amplification of the mycobacterium target via strand displacement amplification (SDA) (see FIG. 5, panel "b"). An ethidium bromide (EtBr) stained agarose gel of the HIV PCR, shown in FIG. 5, panel "a" exhibited excellent amplification product. In FIG. 5, panel "a", well 1 is a molecular weight ladder, wells 2 and 3 are positive aqueous 1000 copy control amplifications, wells 4, 5, 6 and 7 are aluminum oxide solid phase PCR amplifications, wells 8, 9, 10 and 11 are negative aluminum oxide solid phase controls, and wells 12 and 13 are aqueous negative controls. Following the HIV PCR amplification, the aluminum oxide is washed four times with 70% EtOH, dried at 55° C. for 10 minutes, then an SDA amplification of the mycobacterium target is performed. An EtBr stained agarose gel of the SDA amplification also reveals amplification product at equivalent levels to those observed in the aqueous controls (FIG. 5, panel "b"). In FIG. 5, panel "b", wells 1 and 2 are aqueous positive controls, wells 3, 4, 5 and 6 are aluminum oxide solid phase DNA amplifications, wells 7, 8, 9 and 10 are negative aluminum oxide controls, and wells 11 and 12 are aqueous negative controls.

Additional experimental procedures (not shown) showed that the mycobacterium plasmid DNA is bound to aluminum oxide using either the 4 M guanidine thiocyanate buffer or 0.1 N NaOH binding buffers and that SDA amplification occurred on these solid phases.

Alkaline conditions are commonly known to produce single strands. DNA is also single stranded in 4 M guanidine thiocyanate buffer (Thompson and Gillespie, *Analytical Biochemistry*, 163:281-291 (1987), specifically incorporated herein by reference). SDA amplification of DNA bound to aluminum oxide in NaOH or guanidine thiocyanate buffer proceeds without a melt step. These data confirm that in these binding buffers the DNA is bound as single strands and provides for a direct interface between DNA purification with aluminum oxide and isothermal amplification methods requiring a single stranded target nucleic acid.

To illustrate that aluminum oxide is also capable of efficient binding of RNA, the 4 M guanidine binding buffer was used with aluminum oxide to purify HIV directly from an acid citrate dextrose (ACD) plasma specimen of an AIDS patient. This specimen had previously been determined by viral load quantitative PCR to have a titer of $2\times10^4$ RNA copies per milliliter. For aluminum oxide extraction, 0.5 mL of plasma was diluted to 5 mL with 4 M guanidine thiocyanate binding buffer and then gravity filtered onto 40 mg aluminum oxide.

Figure 6:
FIG. 6 is an ethidium bromide stained agarose gel of HIV RNA bound to aluminum oxide in guanidine thiocyanate buffer, followed by solid phase rtTH PCR amplification of the HIV RNA on the aluminum oxide.

FIG. 6 shows excellent PCR product formation detected on an EtBr stained agarose gel following rtTH reverse transcriptase amplification. In FIG. 6, well 1 is a molecular weight ladder, well 2 is a 1000 copy positive aqueous HIV DNA, wells 3, 4 and 5 are rtTH reverse transcriptase amplification products following three separate guanidine thiocyanate buffer/aluminum oxide extractions, wells 6 and 7 are aluminum oxide negative controls, and well 8 is an aqueous negative control. The 4 M guanidine thiocyanate buffer protocol is capable of releasing RNA from HIV virions present in plasma, and these were captured via a high volume (5 mL) gravity filtration onto aluminum oxide in an amplifiable state. Aluminum oxide binds nucleic acids in general.

EXAMPLE 5

DNA Archiving

According to this invention, combining the ability to tightly bind nucleic acid to solid phase matrices with direct solid phase amplification allows for repeated analyses of the same DNA sample an infinite number of times. To illustrate this point, 10 µL of acid citrate dextrose (ACD) blood was bound to aluminum oxide in 4 M guanidine thiocyanate buffer. The bound DNA was then PCR amplified five times, 30 cycles each, using five sequential short tandem repeat (STR) amplifications and five different primer sets (Promega) in the following order: 1) F13B, 2) FESFPS, 3) VWA, 4) CTT multiplex, and 5) FFV multiplex. After the final amplification set, the DNA sample had undergone 150 PCR cycles, in toto.

Figure 7:
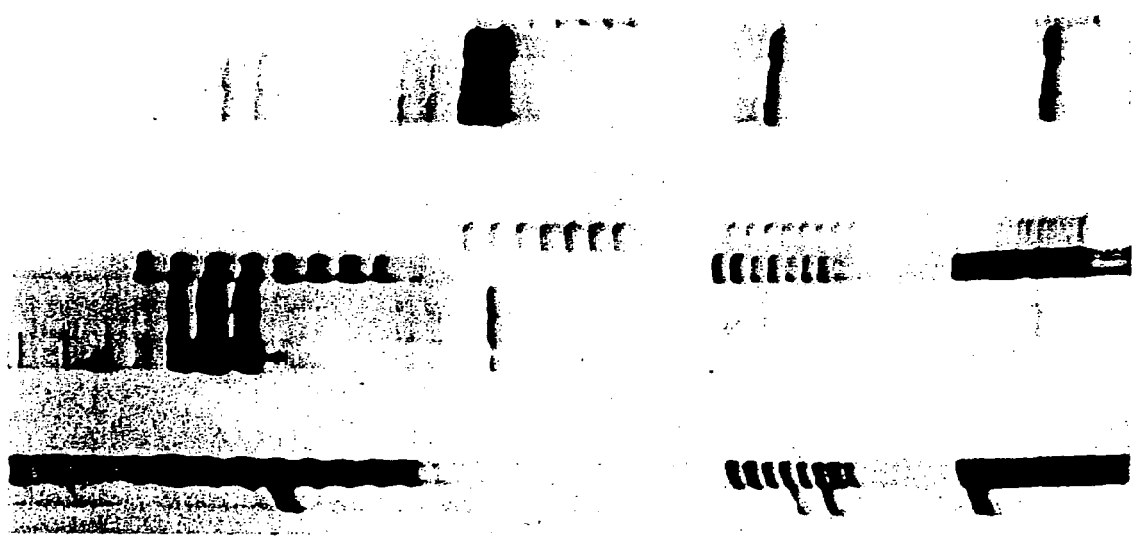
FIG. 7 is a silver stained gel after solid phase amplification of DNA on aluminum oxide with the short tandem repeat marker CTT multiplex and with the short tandem repeat marker FFV multiplex.

FIG. 7 is a silver stained gel depicting the patterns after amplifications with the Promega STE CTT multiplex, which was the fourth gene set amplified, and amplifications with the Promega FFV multiplex, which was the fifth gene set amplified. In FIG. 7, lanes 1, 8, 9 and 16 are allelic ladders, lane 17 is human genomic aqueous positive control, lanes 2, 3 and 4 are the fourth amplification (CTT multiplex) of aluminum oxide-bound DNA, lanes 5, 6 and 7 are the aluminum oxide CTT negative controls, lanes 10, 11 and 12 are the fifth amplifications (FFV multiplex) of aluminum oxide-bound DNA, and lanes 13, 14 and 15 are the aluminum oxide FFV multiplex negative controls. The results, shown in the silver stained gel of FIG. 7, demonstrate that amplification occurred for all five PCRs. These data confirm DNA archiving and repeated solid phase aluminum oxide amplification of the same bound DNA, following 4M guanidine thiocyanate buffer protocol and then amplification by PCR using five sequential short tandem repeat (STM) amplifications (150 total PCR cycles).

In summary, DNA is archived onto aluminum oxide so that it is available for additional amplification analysis. This includes repeat analysis of the same gene, serial amplification of different genes, for example, to detect different infectious agents, or expanded analysis, for example, higher discriminatory power for human identity analysis.

EXAMPLE 6

Buffers That Either Promote or Block Irreversible Binding of Nucleic Acid to Aluminum Oxide Radiolabeled DNA (50 ng) was added to 500 µL aqueous solutions of the various binding buffers listed in Table 2 in the presence of 198 mg aluminum oxide. In order to more accurately measure the exclusive binding of radiolabeled DNA to aluminum oxide, free unincorporated nucleotides that remained following the Biospin 6 purification as described in Example 1 were determined via trichloroacetic acid (TCA) precipitation. As shown in Table 2, using this corrected procedure, DNA bound to aluminum oxide at 100% efficiency in either 4 M guanidine thiocyanate buffer or sodium hydroxide. Certain other substances and/or conditions, such as the addition of blocking buffers, reduce the binding of DNA. In Table 2, for example, these include 10% bovine serum albumin or $K_2HPO_4$ buffer.

TABLE 2

| Binding Buffer | Percent Bound | Percent Unbound |
| --- | --- | --- |
| ddH$_2$O | 20 | 80 |
| 0.1 N NaOH | 110 | 0 |
| 4 M GuSCN | 104 | 0 |
| 10% BSA | 5 | 95 |
| 1 M K$_2$HPO$_4$ | 4 | 96 |
| 10% Triton ™ X-100 | 64 | 36 |
| 10% Tween ™ 20 | 106 | 0 |
| 10% SDS | 12 | 88 |
| 5X SSC | 60 | 40 |

Since both binding and blocking conditions have been defined, it is therefore possible to develop a convenient and specific procedure for first tightly binding specific oligonucleotides or probes to the solid phase matrix, and then changing the reaction conditions by adding a blocking buffer that allows for capture of a specific target by hybridization to the solid phase bound nucleic acid. For example, a first nucleic acid sequence can be tightly bound to a solid phase matrix of this invention by contacting the sample with the matrix in a buffer that allows the first nucleic acid to tightly bind to the matrix. Then, when it is desired to hybridize a second nucleic acid sequence to the bound first nucleic acid sequence, the buffer conditions can be changed to a blocking buffer, such as a phosphate buffer, that allows hybridization of the second nucleic acid to the first nucleic acid while reducing the amount of second nucleic acid that becomes bound to the solid phase matrix. The blocking buffers therefore serve as hybridization buffers with low background signal for hybridizing nucleic acid sequences to the solid phase bound first nucleic acid. After performing the desired manipulation (e.g., amplification, detection, etc.) the hybridized second nucleic acid sequence is then removed. The solid phase bound first nucleic acid can then be reused multiple times.

It is well know that RNA is destroyed in 0.1 N NaOH. Therefore, by using this binding buffer DNA is exclusively captured. Efficient cell disruption and rapid nucleic acid binding with both guanidine thiocyanate buffer and sodium hydroxide buffers is effective for blood, buccal swabs, urine, and HIV virions spiked into plasma or serum. However, for certain infectious organisms, such as *Cryptosporidium parvum*, it is necessary to heat the specimen to 95° C. and include protein reducing agents such as dithiothreitol (DTT) in order to efficiently disrupt the cell (SEQ ID NOS: 1-3; Table 1).

EXAMPLE 7

Figure 8:
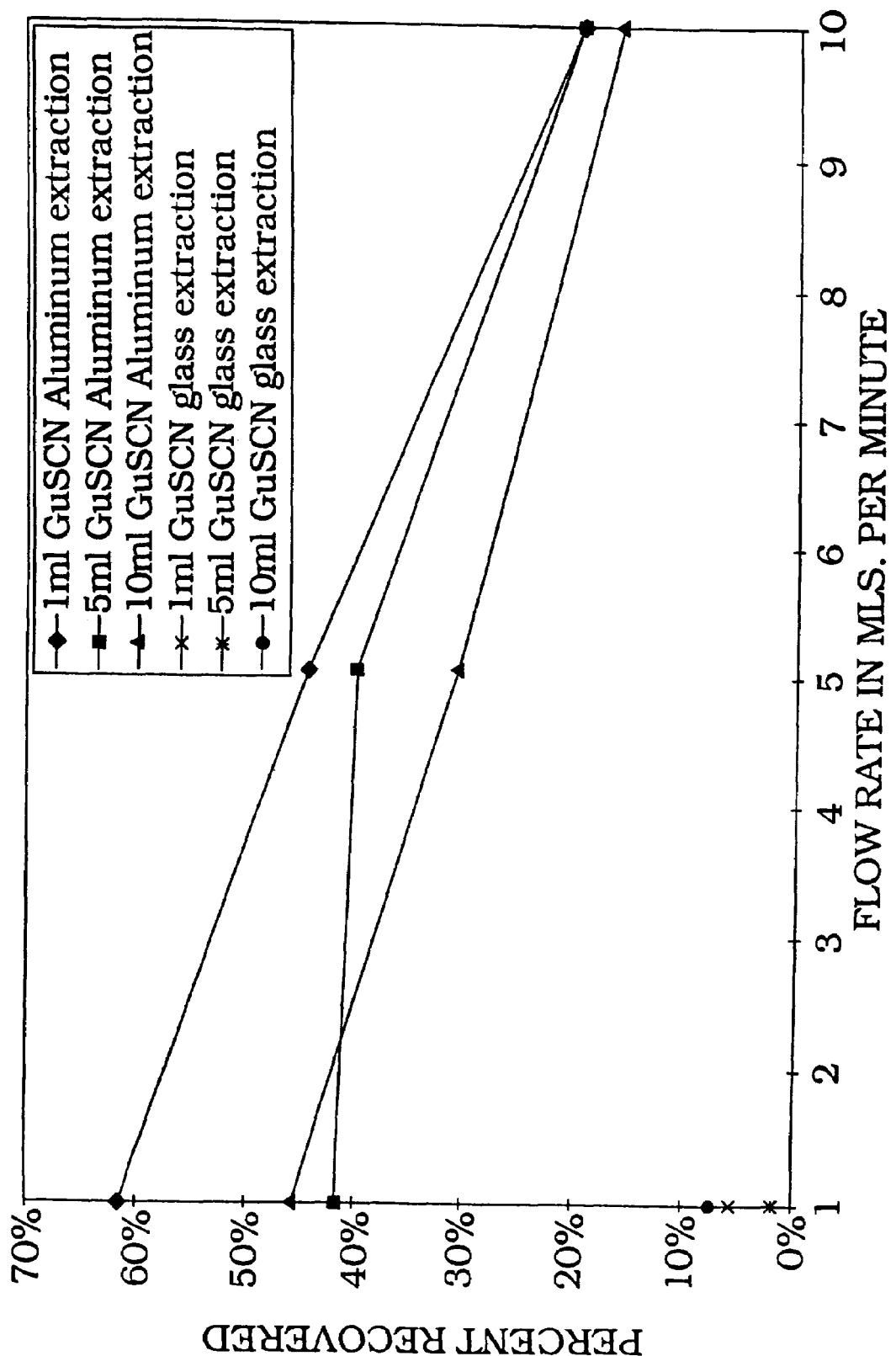
FIG. 8 depicts percent radiolabeled DNA bound to either aluminum oxide or silica dioxide for various starting volumes and at different flow rates.
Figure 9:
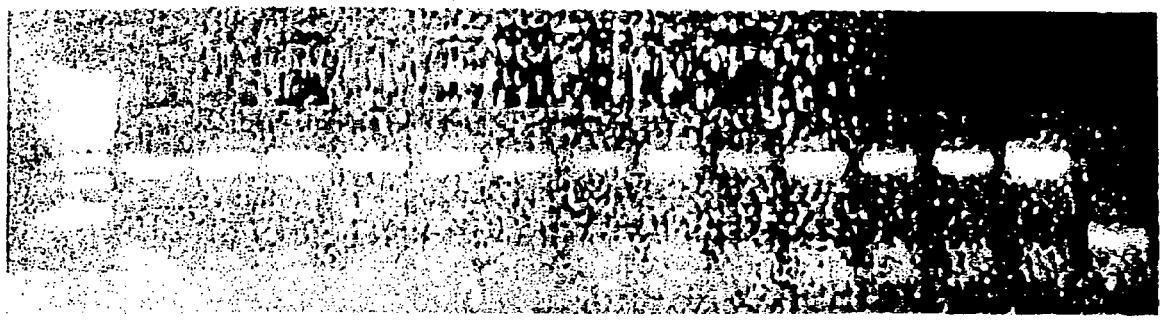
FIG. 9 depicts solid phase PCR amplification as confirmed by ethidium bromide agarose gel using HLA DRbcta primers following tight solid phase capture for different capture times after addition of acid citrate dextrose (ACD) anticoagulated blood in the presence of 0.1 N NaOH and aluminum oxide.

Immediate Binding at High Flow Rate and Incorporation of Aluminum Oxide into PCR Tubes The capability of aluminum oxide (Al$_2$O$_3$) to bind DNA at high flow rates is measured using the same total cpm of radiolabeled DNA suspended in 1 mL, 5 mL, or 10 mL of 4 M guanidine thiocyanate buffer and passing these by either aluminum oxide (Al$_2$O$_3$) or silicon dioxide (SiO$_2$) at measured flow rates. The results, shown in FIG. 8, confirm that aluminum oxide is vastly superior to silicon dioxide. Aluminum oxide (Al$_2$O$_3$) efficiently bound nucleic acid at flow concentration, high volume (10 mL) specimens to the 1 mL specimen with 10-fold higher per ml concentration and ten fold smaller volume. DNA binding is immediate, as illustrated by the experimental results depicted in FIG. 9. Here, 50 μL of acid citrate dextrose (ACD) anticoagulated blood was added to aluminum oxide (Al$_2$O$_3$) in 0.1 N NaOH binding buffer. The HLA DR beta gene was PCR amplified from the solid phase bound DNA either immediately or after permitting various incubation times for the DNA to bind. In FIG. 9, binding as indicated by the efficiency of amplification was identical for the immediate time point (lanes 1-4), the 1-minute time points (lanes 5-8) or the 2-minute time point (lane 14). Lane 13 is the aqueous negative control.

Figure 10:
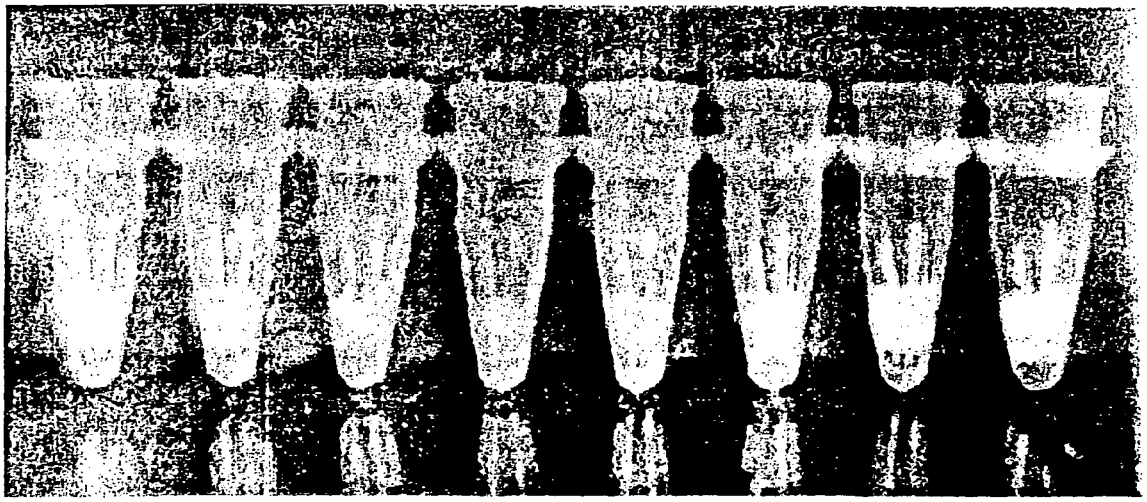
FIG. 10 shows PCR amplification tubes incorporating solid phase matrix for automated nucleic acid extraction.

These experimental results are the basis of an extremely convenient and rapid protocol for automatable nucleic acid extraction that is directly interfaced with PCR amplification. For this, aluminum oxide is adhered, via a silicon or any other adhesive shown not to inhibit PCR, into PCR tubes as shown in FIG. 10. Alternatively, it may be incorporated into a 96 PCR tube plate for higher throughput. Either of these alternatives provides for simple nucleic acid extraction by a protocol comprising: 1) adding binding buffer to the aluminum oxide PCR tube, 2) adding specimen to each tube, mixing and then aspirating liquid to waste, 3) washing by repeat pipetting wash buffer (three times), then aspirating wash buffer to waste, 4) adding PCR amplification master mix, and 5) amplifying in a thermal cycler. The pipetting steps of this protocol are easily automated for high throughput using a robotic system.

EXAMPLE 8

Confirmation of Binding of Pure RNA to Aluminum Oxide (Al$_2$O$_3$)

Figure 11:
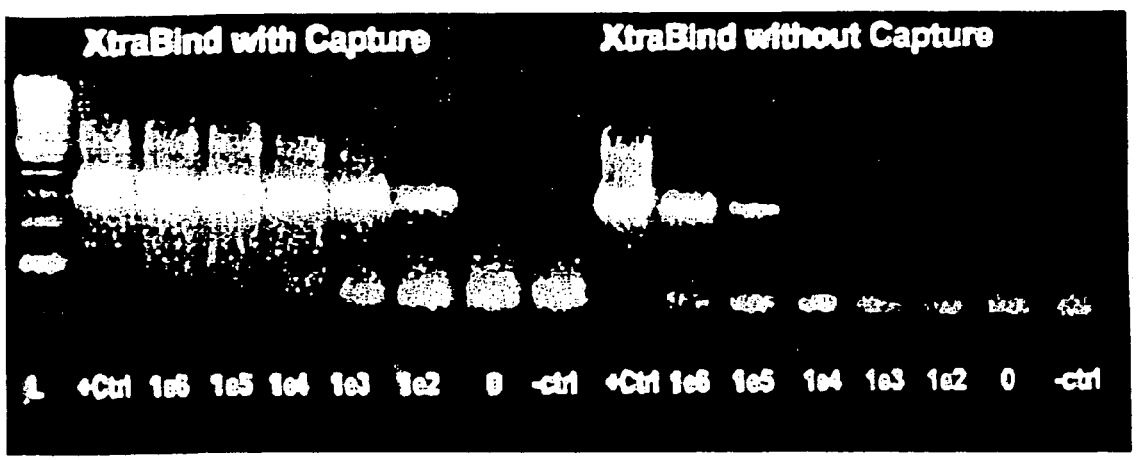
FIG. 11 is an agarose gel after solid phase PCR amplification of a pure RNA target (pAW 109) after either direct binding of the RNA target onto aluminum oxide or after hybridization of the pure RNA target to an oligonucleotide capture probe that is tightly bound to aluminum oxide.

Example 4 described that RNA can be tightly bound to and is amplifiable on aluminum oxide based upon the detection of HIV from a patient plasma specimen. It is possible that this result is due to contaminating proviral DNA in the serum. RNA binding using a pure RNA target confirmed irreversible binding and solid phase amplification. FIG. 11 depicts the results of amplification of a pAW109 pure RNA target bound in 4 M guanidine thiocyanate buffer and rtPCR amplified on the aluminum oxide (Al$_2$O$_3$) solid phase. Binding and amplification of IL-2 mRNA and *Cryptosporidium parvum* dsRNA on aluminum oxide (not shown) were demonstrated in a similar manner.

EXAMPLE 9

Utilization of Tightly Bound Nucleic Acid Probes for Specific Target Capture by Hybridization Experiments performed to determine the limits of detection indicated that detection of DNA bound to aluminum oxide (Al$_2$O$_3$) following PCR amplification requires 1000 copies, and bound RNA requires 103 copies (FIG. 11). Sensitivity of detection was significantly improved to less that 100 copies for either RNA or DNA by binding a nucleic acid probe to a solid phase matrix according to this invention, followed by hybridization of the probe to a target nucleic acid present in a sample. High copy nucleic acid probe of 20-100 base pair length complementary to a sequence adjacent to the desired nucleic acid target was tightly bound to aluminum oxide (Al$_2$O$_3$) in 0.1 N NaOH buffer. After washing, this probe was used to capture the nucleic acid target via hybridization, even in specimens that contain high background levels of nucleic acid. For this procedure, the specimen was disrupted with 4 M guanidine thiocyanate buffer and diluted three fold in the presence of the matrix-bound probe. Hybridization was permitted to occur. Following a wash step, the target was directly PCR amplified. As shown in FIG. 11, this results in limits of detection of between about 10 to 100 copies of the target.

EXAMPLE 10

Capture of Low Copy Targets in High Volume or Pooled Specimens

Figure 12:
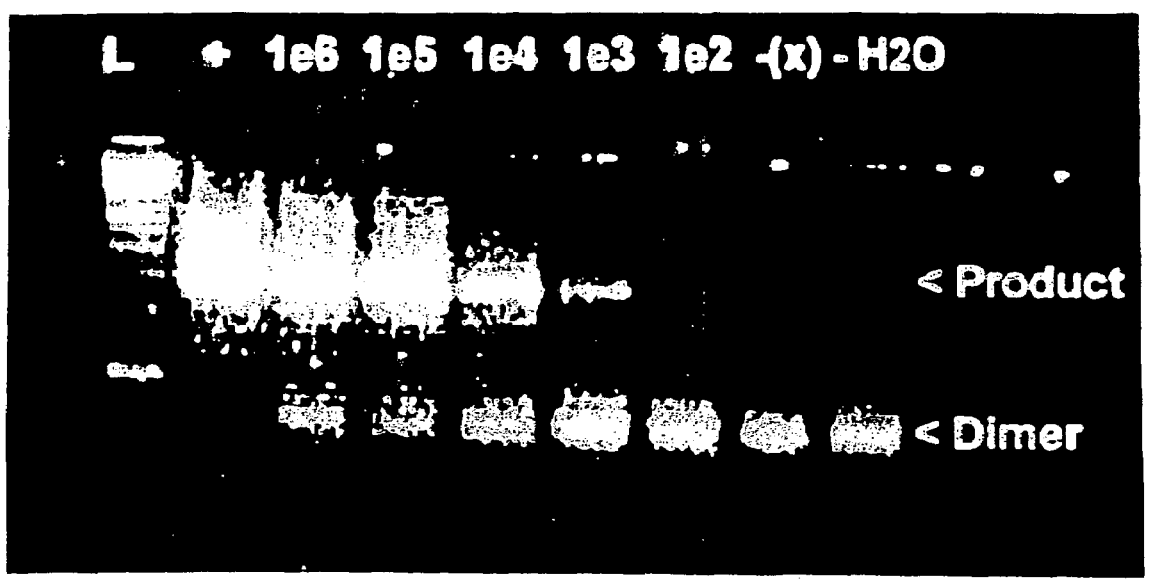
FIG. 12 shows low copy detection of 1000 copies of HIV after dilution with plasma and hybridization to an oligonucleotide capture probe that is tightly bound to aluminum oxide beads.

Hybridization capture by a nucleic acid probe that is tightly bound to aluminum oxide is efficient for the specific selection of target sequences even at high initial specimen volumes. As shown in FIG. 12, 1000 copies of HIV from an AIDS patient plasma specimen were detectable with the hybridization solid phase capture procedures described above, even when diluted to an initial volume of 5.5 mLs with plasma. The plasma was added directly to dry guanidine thiocyanate powder for the extraction in order to minimize dilution. With this adjustment, the final volume for hybridization to the capture bead was 30 mLs. Additionally, positive HIV plasma at 100 µL volume was pooled with an additional 24 negative plasma specimens (100 µL), and was still detected. These pooling experiments confirmed a detection sensitivity of 48 HIV virion copies per milliliter. Similar procedures demonstrated the detection of 100 copies of Cryptosporidium parvum pooled in 30 mLs of water (not shown). The hybridization capture probe protocol, therefore, can be used to screen pooled specimens at a sensitivity almost equivalent to that for an individual specimen, carrying tremendous commercial potential since it will allow highly sensitive pooled specimen testing and providing significant reduction of cost.

EXAMPLE 11

Storage of Nucleic Acid Tightly Bound to Aluminum Oxide

The nucleic acid from 50 µL of acid citrate dextrose (ACD) blood was bound onto aluminum oxide using either the 4 M guanidine thiocyanate buffer or 0.1 N NaOH buffer. The bound nucleic acid was then stored either dry, in 70% EtOH, or in Tris EDTA buffer at room temperature, 4° C., or –20° C. Nucleic acid was generally stable for all of these conditions for three months, and potentially much longer utilizing the instant invention—perhaps indefinitely.

EXAMPLE 12

Identification of Additional Materials Capable of Nucleic Acid Archiving

This Example illustrates that select materials have been identified that perform the generally stated purpose of nucleic acid archiving. These materials bind DNA and RNA with high binding constants, while also allowing enzymatic amplification methods to access the bound nucleic acids for target amplification. To identify materials that can tightly bind nucleic acids, a fluorescent method was designed as a more convenient alternative to the radioisotope experiments described previously. For DNA, synthetic oligonucleotides with a 5' end labeled fluorescent dye, such as fluorescein, were used. For RNA, run-off transcription in the presence of dye-labeled nucleotides with an RNA polymerase was used to generate labeled strands. These fluorescently-labeled strands were mixed with binding buffer, exposed to different materials, and then washed after designated times. Fluorescence emission of the materials with and without binding can be measured, as well as emission from the various solutions (labeled nucleic acids, washes). After confirming binding to a matrix, the capability of the bound nucleic acids to be amplified can be verified with extraction and amplification procedures using DNA or RNA, purified nucleic acids or nucleic acids in various media (blood, cell culture, etc.), and different amplification methods such as PCR, NASBA, and SDA.

One of the preferred solid phase matrices of this invention is alpha-aluminum oxide ($Al_2O_3$), which is sold as a nucleic acid binding matrix under the trademark Xtra Bind™ (Xtrana, Inc., Broomfield, Colo.). It is important to note that aluminum oxide exists in different chemical forms with unique properties associated with each. For the described nucleic acid archiving, alpha aluminum oxide is suitable for binding and amplification in standard conditions. Other forms of aluminum oxide may bind DNA or RNA, but amplification of the bound nucleic acids requires changes in the amplification reaction. For example, PCR amplification of DNA bound to gamma aluminum oxide can be successful if the magnesium ion concentration is increased approximately 50% or more. Increasing the polymerase concentration can also help. Alpha aluminum oxide is sometimes referred to as fused or calcined, but these terms are generally not as specific or well defined as the term "alpha."

In addition to aluminum oxide, particularly alpha aluminum oxide, other materials have been identified as useful nucleic acid archiving matrices. These materials are titanium oxide ($Ti_2O_3$), a thin film aluminum oxide of mixed composition, generally referred to as $Al_xO_y$, and modified zirconium dioxide ($ZrO_2$). To prepare modified $ZrO_2$, the $ZrO_2$ exposed to an acidic or a basic solution, then mixed with DNA and washed, followed by enzymatic amplification has demonstrated amplification of bound DNA. The capabilities of these various materials are demonstrated in FIGS. 13-16.

Figure 13:
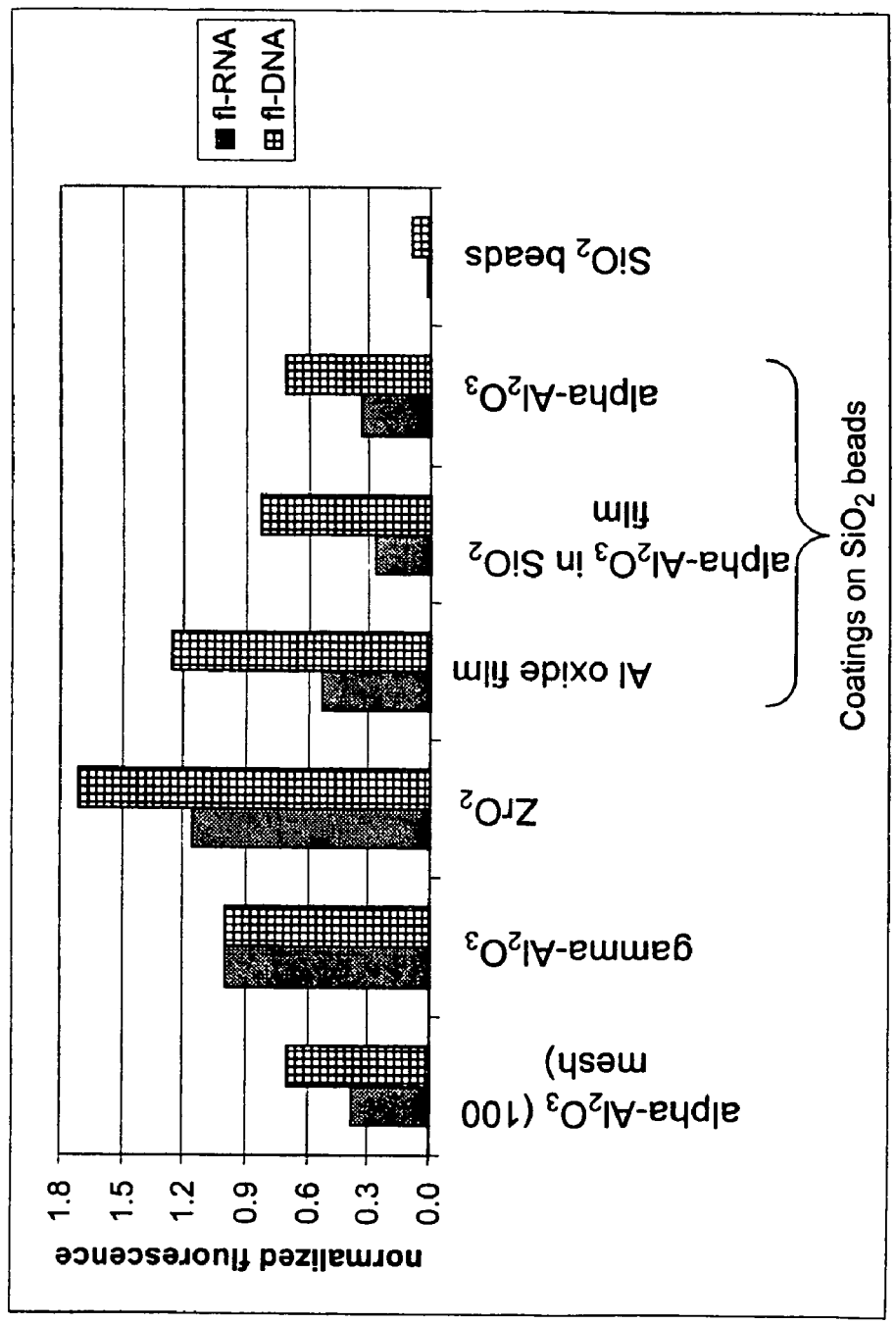
FIG. 13 is a bar graph presenting fluorescent signals from fluorescently labeled DNA and RNA bound to different solid phase materials. The materials were: 100-200 mesh alpha-aluminum oxide (alpha-$Al_2O_3$), gamma-aluminum oxide, zirconium dioxide, a series of $SiO_2$ beads that were either coated or treated, and untreated $SiO_2$ beads.

FIG. 13 is a bar graph presenting fluorescent signals from fluorescently labeled DNA and RNA bound to different solid phase materials. The solid phase materials used in this Example were: 100-200 mesh alpha-aluminum oxide (alpha-$Al_2O_3$), 150 mesh gamma-aluminum oxide, 100-200 mesh zirconium dioxide, glass beads (150-212 µm), glass beads coated with 1000 mesh alpha-$Al_2O_3$, glass beads coated with 1000 mesh alpha-$Al_2O_3$ in a $SiO_2$ thin film, and glass beads having a thin film of aluminum oxide deposited thereon. Glass ($SiO_2$) beads were also used as a minimally binding reference, and the results for DNA and RNA are normalized by their respective gamma-$Al_2O_3$ signals.

Figure 14:
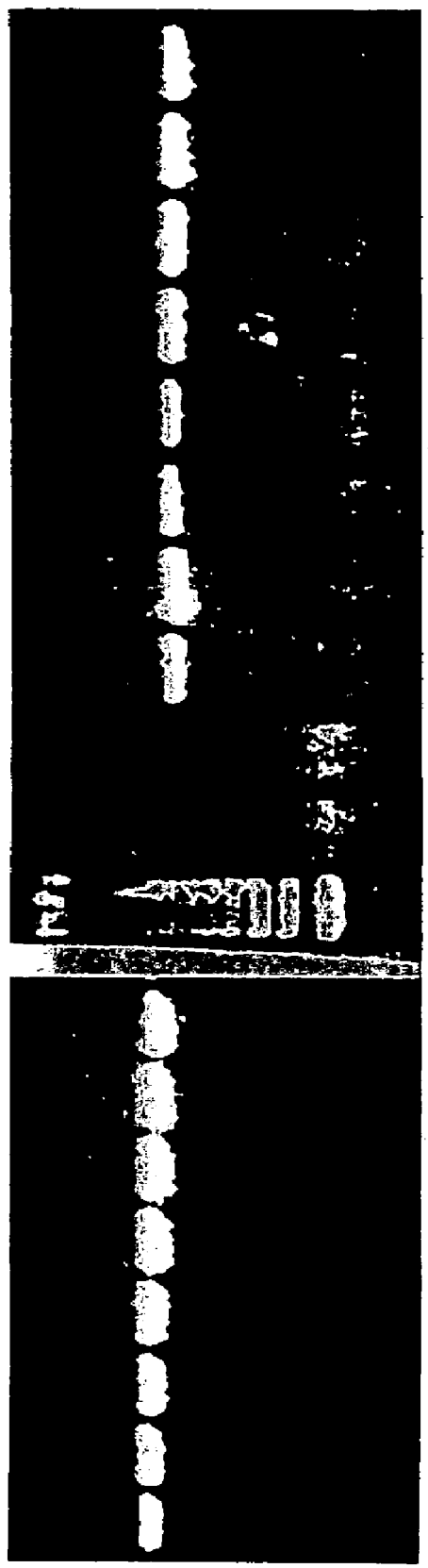
FIG. 14 shows ethidium bromide-stained agarose gels after PCR amplification of DNA bound to different materials. The gels shown were washed four and eight times prior to amplification. The tested materials were Xtra Amp™ tubes (XA), alpha-$Al_2O_3$, $Ti_2O_3$, and a thin film coating of aluminum oxide on $SiO_2$ beads. Duplicate reactions are shown for each matrix and number of washes.

FIG. 14 is ethidium bromide-stained, agarose gels after PCR amplification of DNA bound to different materials. The gels shown were washed four and eight times prior to amplification, and similar results were obtained after the fifth, sixth, and seventh washes. The target DNA was purified, placental DNA, and the amplified region was Homo sapiens G protein-coupled receptor 57 (GPR57). For this figure, the tested materials were 1) PCR tubes coated with aluminum oxide ($Al_2O_3$); 2) alpha-$Al_2O_3$; 3) $Ti_2O_3$; and 4) a thin film coating of aluminum oxide on glass beads. Duplicate reactions are shown for each matrix and number of washes.

Figure 15:
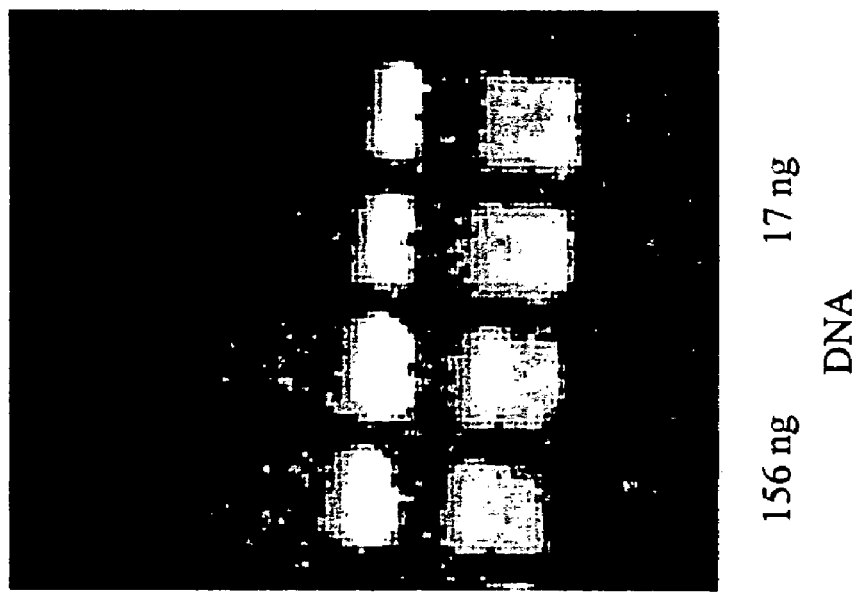
FIG. 15 shows ethidium bromide-stained agarose gels after PCR amplification of DNA bound to a thin film of aluminum oxide coated on the inner walls of glass capillary tubes.

FIG. 15 is ethidium bromide-stained, agarose gels after PCR amplification of DNA bound to the inner walls of glass capillary tubes that were coated with a thin aluminum oxide film. Bound DNA was amplified with rapid thermal cycling for approximately 45 minutes total time. The bound target was purified placental DNA, and the amplified region was the Homo Sapiens G Protein-coupled receptor 57 gene.

FIG. 16 shows lateral flow strips with prominent bands obtained by NASBA amplification of RNA from *Escherichia coli*. *E. coli* dilutions using either PCR tubes coated with $Al_2O_3$ or a $Ti_2O_3$ slurry were processed, and the results shown.

EXAMPLE 13

Alternative Methods for Coating Plastic Surfaces with the Solid Phase Matrix Materials (A) One method of coating plastic surfaces according to this invention involves bringing a heated solid phase matrix in contact with cooled plastic. This permits the partial melting of the plastic and embedding of the solid phase matrix. The solid phase matrix is heated to from 700° C. to 800° C. in a crucible, then poured onto or into the plastic materials (e.g. PCR tubes) that have been cooled to a temperature between about 0° C. and 10° C. For example, the plastic material can be placed in an ice bath (4° C.). Excess solid phase matrix is tapped out and the tubes packaged. Variations to this general heating and melting method, such as utilizing a manifold for coating multiple tubes simultaneously, have also been developed.

(B) In addition to melting the solid phase matrix into the PCR tubes or other plastic materials, methods to deposit thin film coatings on the surface of the plastic have been identified. Using conventional treatment and deposition methods such as plasma etching, chemical vapor deposition (CVD), and thermal evaporation, metal oxide thin-films can be deposited and bound to the underlying plastic material. Adjusting the deposition conditions leads to films that bind nucleic acids and allow amplification of the bound DNA or RNA.

(C) As a variation, the plastic surfaces can be chemically activated, for example, by plasma etching or strong acid/base treatment and a liquid metal oxide precursor such as aluminum s-butoxide or another alkoxy metal reagent can be introduced to react with the activated plastic surface. Methods of activating plastic surfaces are known in the art and need not be described in further detail. This approach can also create the desired binding and amplification coatings.

EXAMPLE 14

Methods for Coating A Solid Phase Matrix onto an Oxide Surface

Solid phase matrices can be deposited on glass surfaces in capillaries, slides, and other formats, as well as other oxide surfaces by several methods as described below.

(A) In one embodiment, aluminum oxide granules of large or small dimensions were adhered to the glass surfaces with acidic or basic conditions that promote hydrolysis, followed by drying. An example of an acidic solution includes a solution containing, by volume, 95% ethanol, 0.5% concentrated hydrochloric acid (HCl), and 4.5% water.

(B) In another embodiment, aluminum oxide granules were deposited on glass surfaces by mixing the aluminum oxide with a sol comprising silicon dioxide, aluminum oxide, or metal oxide precursors such as tetramethoxysilane, tetraethoxysilane, or aluminum s-butoxide, allowing the mixture to gel on the glass surface, and drying the mixture. This provided a film of aluminum oxide granules in a metal oxide binder.

(C) In another embodiment, $Ti_2O_3$ granules were deposited on glass surfaces by Methods A and B of this Example.

(D) In addition to depositing existing aluminum or titanium oxide granules, metal oxide films were deposited on glass substrates by reacting metal oxide precursors, such as aluminum s-butoxide or titanium ethoxide in a solution phase reaction in which the precursor hydrolyzed and forms metal hydroxides. The metal hydroxides are then condensed with each other, leading to covalent bonding to the oxide layer of the glass or other underlying metal oxide substrate. For example, an aluminum oxide sol was prepared by hydrolysis and peptization of aluminum s-butoxide following the procedure described by A. C. Pierre and D. R. Uhlmann (*J. Am. Ceram. Soc.* 70:28-32 (1987)). The glass surface is then exposed to this solution, followed by drying. This resulted in a thin film coating of aluminum oxide having a mixed aluminum and oxygen composition. For example, certain regions of the film may contain $Al_2O_3$, other regions may comprise $Al_{2.3}O_{3.1}$, etc.

The coatings described in this example can be deposited by any number of suitable methods known in the art, including but not limited to, dipping, immersing, spin casting, or by similar methods of exposing the substrate to the liquid suspension/sol of materials.

EXAMPLE 15

Long Term Storage of Archived DNA and RNA (A) In Example 11, the storage of genomic DNA extracted from blood was confirmed to be stable for three months. This study has now been extended to 18 months. Even after the sample described in Example 11 was stored dry for 18 months, robust amplification occurred (data not shown).

(B) A similar experiment was designed to determine the capability of aluminum oxide to permit stable storage of RNA. RNA was obtained from an *E. coli* slt 1 only lab strain, and purified with the Qiagen RNeasy Maxi Kit™. 1:2, 1:4, and 1:10 dilutions of the starting RNA extract (316 ng) were made and then bound to Xtra Amp™ tubes by adding 50 mL of 10×PCR buffer without $MgCl_2$ and 5 ml of each RNA dilution. After a 30 minute incubation, the supernatant was removed, the tubes were allowed to air dry for 5-10 minutes. All tubes were capped and stored at either room temperature, 4° C., or −20° C. Tubes were removed at 1 week intervals, and an *E. coli* sz and slt1 multiplex, NASBA master mix was added. A 90 minute NASBA reaction at 42° C. followed, with the following conditions: 80 mM Tris-HCl, (pH 8.5), 50 mM KCl, 12 mM $MgCl_2$, 10 mM DTT, 1 mM dNTP mix, 2 mM rNTP mix, 200 nM primer mix, 15% sorbitol, and 15% DMSO. The results were visualized by lateral flow detection using the methods described in U.S. Pat. No. 5,989,813, which is specifically incorporated herein by reference. The purified RNA was stable for the 8 weeks when stored at 4° C. and −20° C., and some degradation was apparent after 8 weeks when stored room temperature, particularly at the higher 1:10 dilution.

EXAMPLE 16

Solution-Phase Amplification of Nucleic Acids Displaced from the Matrix

Some applications such as genotyping can benefit from simplified sample preparation and solid phase archiving according to the methods of this invention described above. In another embodiment, amplification is performed in solution using a purified nucleic acid sample, rather than on the solid phase. This example provides such a method using the solid phase matrix materials described herein. Although the nucleic acid targets are tightly bound to the solid phase, a small percentage of the nucleic acids are released (displaced) into solution as purified nucleic acid when the matrix is washed with TE buffer, water, or other suitable buffers. This solution can then be used in a standard enzymatic amplification reaction. Multiple rounds of release and amplification are feasible, allowing multiple amplification targets to be analyzed individually.

Figure 17:
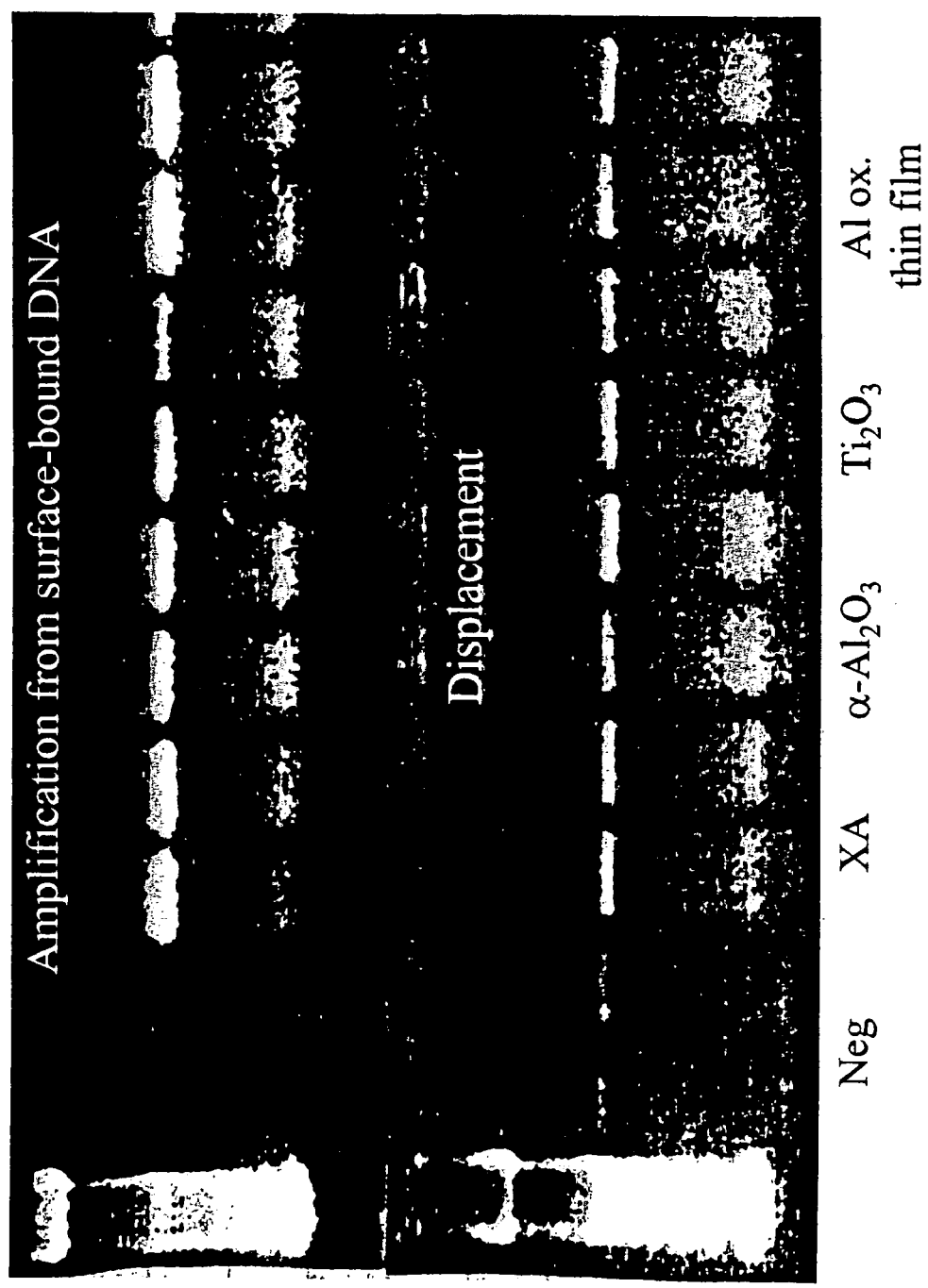
FIG. 17 shows ethidium bromide-stained agarose gels after PCR amplification of matrix-bound DNA (upper portion of gel) and DNA displaced from the surface of the indicated matrix (lower portion of gel). Tested materials were: Xtra Amp™ tubes (XA), alpha-$Al_2O_3$, $Ti_2O_3$, and glass beads having a thin film coating of aluminum oxide.

The standard displacement procedure included placing a solution of blood mixed with lysis buffer in an Xtra Amp™ tube or a tube containing 5 to 10 μL of $Al_2O_3$, $Ti_2O_3$, or coated glass beads, and following standard procedures for incubation and washing. After washing, 50 to 100 μL of TE buffer (Tris HCl/EDTA) were added to the tube. The solution was incubated for about 30 minutes, and the TE solution was removed. Aliquots (5-10 μL) of the removed TE solution containing the displaced DNA were then mixed with a conventional PCR master mix (primers, enzymes, buffers, etc.) and temperature cycled. The procedure of adding TE buffer and removing aliquots was repeated at least five times, resulting in consistent and accurate amplification. FIG. 17 shows an ethidium bromide-stained agarose gel after PCR amplification of the displaced nucleic acid ("Displacement") according to this Example, as well as solid phase amplification of nucleic acid bound to the following solid phase matrix materials: (1) Xtra Amp™ (XA) tubes; (2) 100 to 200 mesh alpha aluminum oxide ($\alpha$-$Al_2O_3$); (3) $Ti_2O_3$, and (4) aluminum oxide thin films. In the example shown in FIG. 17, the bound target was purified placental DNA, and the amplified region was the Homo Sapiens G Protein-coupled receptor 57 gene.

EXAMPLE 17

Methods for Multiple PCR Amplifications Using the Same Archived Matrix

According to the present invention, archived nucleic acid samples present an opportunity to repeatedly process the same sample immediately or over an extended time period. The archived samples further allow for the investigation of the same amplified region multiple times and/or the investigation of a series of different targets.

(A) Protocols have been developed to allow repeated amplification of the same matrix-bound target. To repeatedly amplify the same target region, purified nucleic acid or lysed biological samples are introduced to an Xtra Amp™ tube or an alternative tube containing a slurry of aluminum oxide, titanium oxide, or other granules. Standard binding and wash procedures are followed. Primers and PCR mix for the target amplicon are then added to the tube, and a standard 32 to 40 cycle PCR reaction is performed. The product solution is removed, and the tube washed with a wash buffer at 95° C. For additional rounds to amplify the same target, primers and PCR mix are added, and a much smaller number of amplification cycles are necessary.

Figure 19:
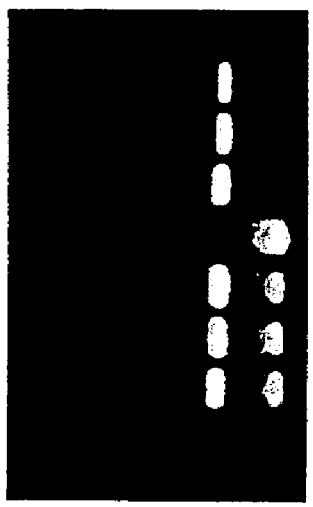
FIG. 19 shows an ethidium bromide-stained agarose gel after re-amplification (10 and 15 cycles) of the same target region (HLA-DRβ) described in FIG. 18.
Figure 18:
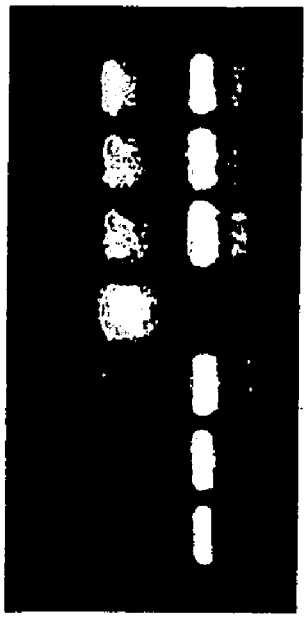
FIG. 18 shows an ethidium bromide-stained agarose gel of an initial PCR amplification (35 cycles) of the same target region (HLA-DRβ) from the same matrix-bound DNA.
Figure 20:
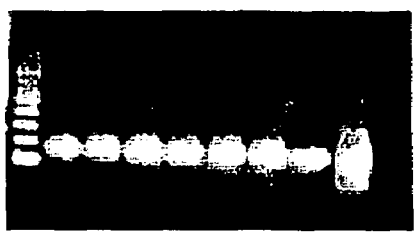
FIG. 20 shows an ethidium bromide-stained agarose gel of serial PCR amplification reactions of different regions of the same matrix-bound DNA. The amplified target is HUGALPCR2.
Figure 21:
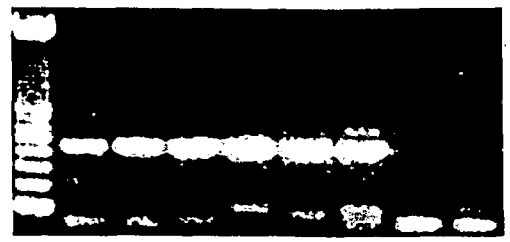
FIG. 21 shows an ethidium bromide-stained agarose gel of serial PCR amplification reactions of different regions of the same matrix-bound DNA. The amplified target is HGH PCR5.
Figure 22:
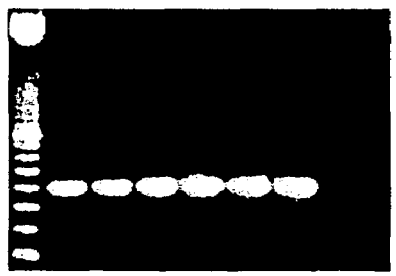
FIG. 22 shows an ethidium bromide-stained agarose gel of serial PCR amplification reactions of different regions of the same matrix-bound DNA. The amplified target is HDYST3.
Figure 23:
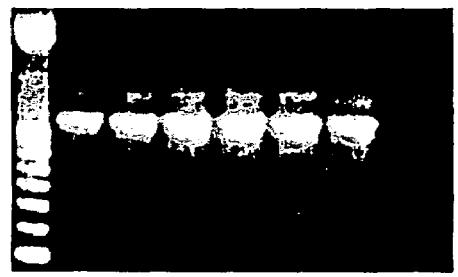
FIG. 23 shows an ethidium bromide-stained agarose gel of serial PCR amplification reactions of different regions of the same matrix-bound DNA. The amplified target is HLA A.

FIGS. 18 and 19 show ethidium bromide-stained agarose gels of repeat amplification of the same region of matrix-bound DNA. Genomic DNA was extracted from whole blood (human) using Xtra Amp™ tubes. PCR amplification (35 cycles) was performed to amplify the HLA-DR beta gene using standard PCR conditions for amplification of this gene. (FIG. 18) The Xtra Amp™ tubes were then incubated at 95° C. for 10 minutes with a wash buffer (150 mM LiCl, 10 mM Tris-HCl, 1 mM EDTA, and 0.10% Tween-20). The wash buffer was removed and fresh PCR amplification reagents were added to re-amplify HLA-DRβ. In the second amplification reaction, the PCR reagent concentrations and cycle parameters were the same as with the initial amplification reaction, with the exception that the number of PCR cycles was decreased. FIG. 19 shows the gels after 10 and 15 PCR cycles. Approximately ten cycles were sufficient to generate amplicons that were clearly visible and relatively clean when viewed on an ethidium bromide stained, agarose gel (FIG. 18).

(B) To amplify a series of different nucleic acid targets, the first round followed standard procedures: samples were introduced to a container such as a PCR tube coated with a solid phase matrix (e.g., aluminum oxide). Standard binding and wash procedures were followed. Primers and PCR mix for the target amplicon were then added to the tube, and a standard 32 to 40 cycle PCR reaction was performed. Subsequent rounds followed the same basic procedure, except that new primers for different targets were used, and each round was preceded by a high temperature (nominally 95° C.) incubation and wash to remove older, hybridized primer and product. Several different amplicons have been generated with this procedure.

FIGS. 20, 21, 22, and 23 show ethidium bromide-stained agarose gels of serial PCR amplification reactions of different regions of the same matrix-bound DNA. Genomic DNA was extracted from whole blood (human) in Xtra Amp™ tubes. PCR amplification was performed to amplify one gene using standard PCR reaction conditions for amplifying the gene. The tubes were then incubated at 95° C. for 10 minutes with a wash buffer (150 mM LiCl, 10 mM Tris-HCl, 1 mM EDTA, and 0.10% Tween-20). The wash buffer was removed and fresh PCR amplification reagents were added to the tubes to amplify another gene using standard PCR reaction conditions for that gene. The heat incubation with wash buffer and standard PCR reaction conditions were repeated for amplification of several different regions of the matrix-bound DNA. The amplified targets shown in FIGS. 20, 21, 22 and 23 are HUGALPCR2, HGH PCR5, HDYST3, and HLA A, respectively.

EXAMPLE 18

Genome-Wide Sample Boost Using Random Primers and an Initial, Multiplexed Amplification Step (A) The nucleic acids bound to the solid phase can be amplified with multiple primers simultaneously, as well as with a single primer set. By amplifying with multiple primers, a number of different amplicons can be generated simultaneously. Although the conditions for each primer set are not necessarily optimal and result in uneven amplification, the resulting solution can then be used for further, more specific amplifications of a particular target.

(B) A procedure that performs an initial, limited cycle number "boost" in the presence of multiple primers has been described in copending U.S. patent application Ser. No. 09/589,560 to Gerdes, et al., filed Jun. 6, 2000, entitled "Methods of Multiplexing Amplification Reactions," which is specifically-incorporated herein by reference. In this method, a two-step multiplex amplification reaction is performed, where the first step truncates the standard initial multiplex amplification round to "boost" the sample copy number by only a 100-1000 fold increase in the target. Following the first step the product is divided into optimized secondary single amplification reactions, each containing one of the primer sets that were used previously in the first or multiplexed booster step.

Thus, an alternative embodiment of the present invention generalizes the collection of "boost" primers. That is, the method of this invention replaces the collection of primer sets specific to the amplicon targets of later rounds with a collection of random primers. After the "boost" with random primers, the pre-amplified sample was divided into aliquots. Each aliquot was mixed with a primer set and reaction mix specific for an individual target. In this example, a collection of random 9-mers (Stratagene) was used, although other collections of random 9-mers or other primer lengths should also work given that basic rules of hybridization and amplification, such as thermal stability are followed. For this application, the term "random" means that a sufficiently large collection of diverse primers is grouped, so that the entire, or at least a large fraction of, the genome is amplified during the "booster" step.

Figure 24:
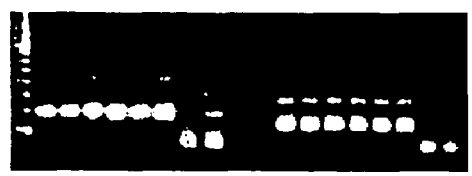
FIG. 24 shows an ethidium bromide-stained agarose gel of specific PCR amplified targets after an initial "booster" step using a collection of random amplification primers. The amplified targets shown in FIG. 24 are HUGALPCR 2 and GAPDH14.
Figure 25:
FIG. 25 shows an ethidium bromide-stained agarose gel of a specific PCR amplified target after an initial "booster" step using a collection of random amplification primers. The amplified target shown in FIG. 25 is HGH-PCR5.
Figure 26:
FIG. 26 shows an ethidium bromide-stained agarose gel of a specific PCR amplified target after an initial "booster" step using a collection of random amplification primers. The amplified target shown in FIG. 26 is HDYST3.

FIGS. 24, 25, and 26 show ethidium bromide-stained agarose gels of specific PCR amplified targets after an initial "booster" step using a collection of random amplification primers. Genomic DNA was extracted from whole blood (human) in Xtra Amp™ tubes. PCR amplifications were performed using random 9-mer primers in the PCR reaction mixture and a moderately stringent PCR program that ran for 10 cycles of the program. Following this "booster PCR", 5 μL of the PCR reaction mixture was aliquoted into individual PCR reactions ("secondary PCR reactions"). Each of these secondary PCR reactions contained a PCR primer pair as would be used in a standard PCR reaction, and each was subjected to a standard PCR cycling program. The amplified targets shown in FIG. 24 are HUGALPCR 2 and GAPDH14, the amplified target shown in FIG. 25 is HGH-PCR5, and the amplified target shown in FIG. 26 is HDYST3.

While the above description contains many specificities, these specificities should not be construed as limitations on the scope of the invention, but rather exemplification of the preferred embodiment thereof. That is to say, the foregoing description of the invention is exemplary for purposes of illustration and explanation. Without departing from the spirit and scope of this invention, one skilled in the art can make various changes and modifications to the invention to adapt it to various usages and conditions. As such, these changes and modifications are properly, equitably, and intended to be within the full range of equivalence of the following claims. Thus, the scope of the invention should be determined by the appended claims and their legal equivalents, rather than by the examples provided herein.

---

We claim:

1. A method of amplifying one or more target nucleic acids, comprising:
   a) contacting a sample containing said one or more target nucleic acids with a solid phase matrix and a buffer that allows said one or more target nucleic acid sequences to become bound to said matrix as single-stranded target nucleic acid, wherein said matrix is a specific binding material having one or more electropositive materials rendered hydrophilic;

b) contacting said matrix-bound target nucleic acid with a set of primer nucleic acid sequences and a buffer that allows said primer sequences to hybridize to said matrix-bound target nucleic acid; and c) amplifying said one or more target nucleic acid to produce an amplified reaction mixture, wherein said target nucleic acid sequence remains bound to said matrix.

2. The method of claim 1, wherein said buffer in step (b) reduces binding of said primer set to said solid phase matrix.

3. The method of claim 1, wherein said electropositive material comprises elements selected from the group consisting of aluminum, titanium, zirconium, hafnium, scandium, yttrium, lanthanum, vanadium, tantalum, chromium, molybdenum, tungsten, boron, gallium, indium, germanium, tin, and lead.

4. The method of claim 3, wherein said matrix is selected from the group consisting of aluminum oxide, titanium oxide ($Ti_2O_3$), and modified zirconium dioxide ($ZrO_2$).

5. The method of claim 1, wherein said matrix is selected from the group consisting of alpha aluminum oxide, gamma aluminum oxide and an aluminum oxide thin-film of mixed composition.

6. The method of claim 1, wherein said matrix is $Ti_2O_3$.

7. The method of claim 1, wherein said matrix is modified $ZrO_2$.

8. The method of claim 1, wherein said buffer in step (a) is selected from the group consisting of guanidine thiocyanate-based buffers, alkaline buffers, lithium chloride, and detergent based buffers.

9. The method of claim 1, wherein said buffer in step (b) is a phosphate buffer.

10. The method of claim 1, wherein said target nucleic acid is selected from the group consisting of double stranded DNA, single stranded DNA, RNA, or PNA.

11. The method of claim 1, wherein said target nucleic acid is double stranded DNA and said buffer in step (a) allows said DNA to be bound to said matrix as single stranded DNA.

12. The method of claim 1, wherein said amplification methodology is selected from the group consisting of PCR, SDA, NASBA, IsoCR, CRCA, Q beta replicase, branched chain DNA, RT-PCR, and unwinding coil amplification.

13. The method of claim 1, further comprising repeating steps (b) and (c) one or more times.

14. The method of claim 1, wherein said sample comprises two or more target nucleic acids and said two or more target nucleic acids are amplified in series.

15. The method of claim 1, wherein said target nucleic acid contains multiple target nucleic acid sequences, said method further comprising contacting said matrix-bound target nucleic acid in step (b) with multiple primer sets to pre-amplify said multiple target sequences, wherein said multiple target sequences are amplified simultaneously.

16. The method of claim 15, further comprising:
(d) dividing said pre-amplified reaction mixture of step (c) into a plurality of aliquots;
(e) adding at least one of said primer sets to each of said aliquots; and
(f) amplifying said aliquots.

17. The method of claim 1, wherein said solid phase matrix is coated on the surface of a substrate.

18. The method of claim 17, wherein said substrate is a glass or polymeric material.

19. The method of claim 17, wherein said substrate is in the shape of tubes, plates, membranes, capillaries, slides, beads, microparticles, fibers, microchannels, and microarrays.

* * * * *